United States Patent
Hayakawa et al.

(10) Patent No.: US 9,494,544 B2
(45) Date of Patent: Nov. 15, 2016

(54) HYBRID SENSOR

(71) Applicant: TOKAI RUBBER INDUSTRIES, LTD., Aichi-ken (JP)

(72) Inventors: Tomonori Hayakawa, Aichi-ken (JP); Hitoshi Ukai, Aichi-ken (JP)

(73) Assignee: SUMITOMO RIKO COMPANY LIMITED, Aichi (JP)

( * ) Notice: Subject to any disclaimer, the term of this patent is extended or adjusted under 35 U.S.C. 154(b) by 341 days.

(21) Appl. No.: 14/227,335

(22) Filed: Mar. 27, 2014

(65) Prior Publication Data

US 2014/0210490 A1 Jul. 31, 2014

Related U.S. Application Data

(63) Continuation of application No. PCT/JP2013/053252, filed on Feb. 12, 2013.

(30) Foreign Application Priority Data

Mar. 2, 2012 (JP) ................. 2012-046224

(51) Int. Cl.
  *G01N 27/22* (2006.01)
  *G01L 1/14* (2006.01)
  *G06F 3/044* (2006.01)
  *G06F 3/041* (2006.01)

(52) U.S. Cl.
  CPC ................. *G01N 27/22* (2013.01); *G01L 1/14* (2013.01); *G06F 3/044* (2013.01); *G06F 3/0414* (2013.01); *G06F 3/0416* (2013.01); *G06F 2203/04106* (2013.01)

(58) Field of Classification Search
  None
  See application file for complete search history.

(56) References Cited

U.S. PATENT DOCUMENTS

| 8,770,045 B2 | 7/2014 | Murayama et al. |
| 2008/0211519 A1* | 9/2008 | Kurumado ............... G01D 5/24 324/688 |

(Continued)

FOREIGN PATENT DOCUMENTS

| JP | 06-060857 | 8/1994 |
| JP | 2011-081578 | 4/2001 |
| JP | 2005-353565 | 12/2005 |

(Continued)

OTHER PUBLICATIONS

International Preliminary Report on Patentability for PCT/JP2013/053252, mailed Sep. 2, 2014.

(Continued)

*Primary Examiner* — Walter L Lindsay, Jr.
*Assistant Examiner* — Jas Sanghera
(74) *Attorney, Agent, or Firm* — Greenblum & Bernstein, P.L.C.

(57) ABSTRACT

A hybrid sensor includes a proximity sensor section and a load sensor section. The proximity sensor section includes a first base material, a plurality of first front-side electrodes, a plurality of first back-side electrodes, and a protective layer. Each of these members is made of an elastomer. The proximity sensor section detects the approach and coordinates of an object to be detected, based on a change in capacitance between the first front-side electrode and the first back-side electrode which is caused by the approach of the object to be detected. The load sensor section detects pressing and coordinates of the object to be detected, based on a load that is applied from the object to be detected via the proximity sensor section.

10 Claims, 18 Drawing Sheets

(56) References Cited

U.S. PATENT DOCUMENTS

| | | | | |
|---|---|---|---|---|
| 2010/0308844 A1* | 12/2010 | Day | ................ | G06F 3/045 324/663 |
| 2011/0163982 A1* | 7/2011 | Wadia | ................ | G06F 3/044 345/173 |

FOREIGN PATENT DOCUMENTS

| JP | 2006-134243 | 5/2006 |
|---|---|---|
| JP | 2006-236296 | 9/2006 |
| JP | 2008-072862 | 3/2008 |
| JP | 2008-225980 | 9/2008 |
| JP | 2011-048541 | 3/2011 |
| JP | 2011-209785 | 10/2011 |
| JP | 2012-7988 | 1/2012 |

OTHER PUBLICATIONS

International Search Report in PCT/JP2013/053252, dated May 14, 2013.
Japan Office action, dated Apr. 7, 2015 along with an English translation thereof.
Partial English translation of JP2006-134243.
Partial English translation of JP2008-225980.

* cited by examiner

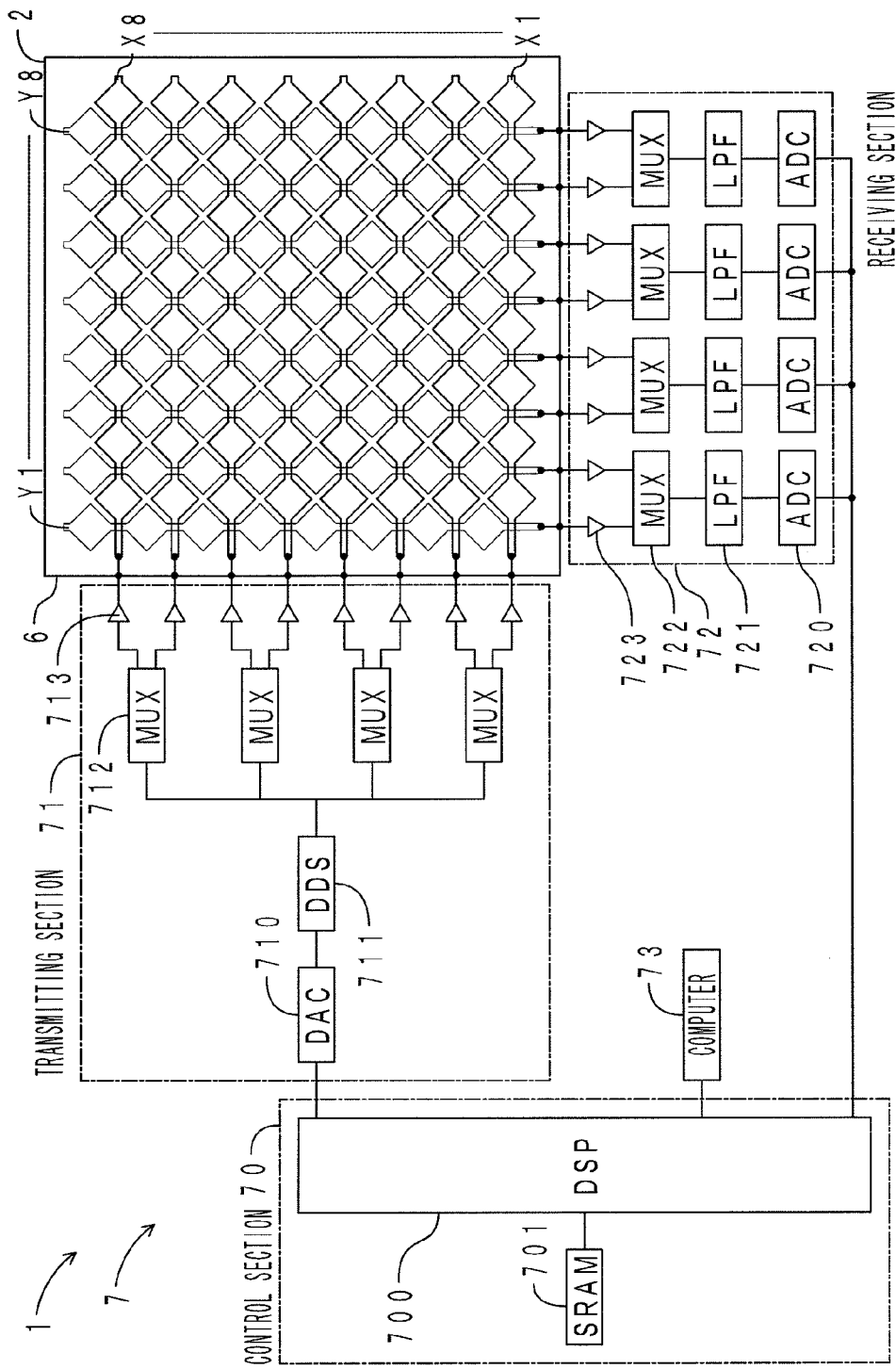
F I G. 5

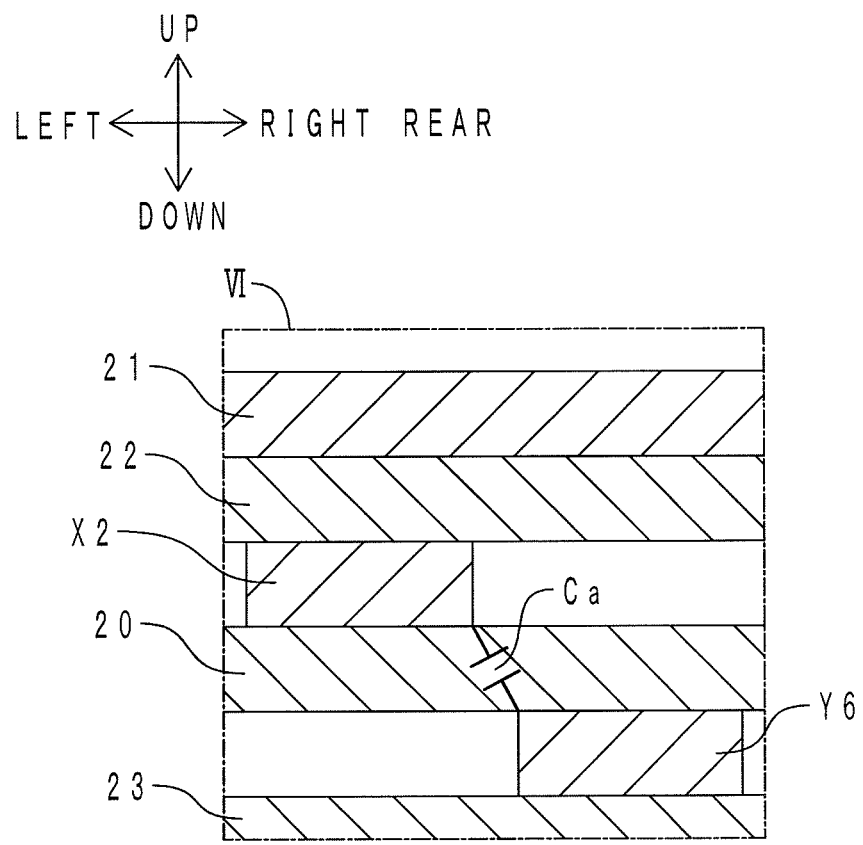
F I G. 6 A

HYBRID SENSOR

CLAIM FOR PRIORITY

This application is a Continuation of PCT/JP2013/053252 filed Feb. 12, 2013, and claims the priority benefit of Japanese application 2012-046224, filed Mar. 2, 2012, the contents of which is expressly incorporated by reference herein in its entirety.

TECHNICAL FIELD

The present invention relates to hybrid sensors for use in touch panels, touch screens, etc.

BACKGROUND ART

Proximity sensors can detect the approach (including contact) of a human body (e.g., a finger) and coordinates of the finger in a planar direction. Load sensors can detect pressing of the finger and coordinates of the finger in the planar direction. The approach, pressing, and coordinates of the finger can be detected by combining the proximity sensor with the load sensor.

In view of this, Patent Document 1 discloses a detection sensor capable of switching between a proximity sensor and a load sensor. Patent Document 2 discloses a hybrid sensor in which a proximity sensor and a load sensor are stacked in the front-back direction.

RELATED ART DOCUMENTS

Patent Documents

Patent Document 1: Japanese Patent Application Publication No. 2011-209785 (JP 2011-209785 A)
Patent Document 2: Japanese Patent Application Publication No. 2005-353565 (JP 2005-353565 A)

SUMMARY OF THE INVENTION

Problem to be Solved by the Invention

However, both of these sensors include a hard layer that is less likely to be locally deformed. For example, the detection sensor of Patent Document 1 includes an upper substrate made of synthetic resin and a lower substrate made of synthetic resin or glass. The hybrid sensor of Patent Document 2 includes a flexible sheet made of an insulating resin film. A load applied from the finger therefore spreads in the planar direction as it is transmitted in the hard layer. This reduces the pressing amount (stroke amount) associated with pressing of the finger, which makes it more difficult for the operator to tactually feel the pressing stroke. Moreover, detection accuracy of the coordinates of the finger decreases because the load spreads in the planar direction.

A hybrid sensor according to the present invention was completed in view of the above problems. It is an object of the present invention to provide a hybrid sensor that is capable of detecting the approach, pressing, and coordinates of an object to be detected, that makes it easier for the operator to tactually feel a stroke, and that has high coordinate detection accuracy.

Means for Solving the Problem (1) In order to solve the above problems, a hybrid sensor according to the present invention is characterized by including: a proximity sensor section that includes a first base material having insulating properties and made of an elastomer, a plurality of first front-side electrodes disposed on a front side of the first base material, having conductive properties, and made of an elastomer, a plurality of first back-side electrodes disposed on a back side of the first base material, having conductive properties, and made of an elastomer, and a protective layer disposed on a front side of the plurality of first front-side electrodes, having insulating properties, and made of an elastomer, and that detects approach and coordinates of an object to be detected, based on a change in capacitance between the first front-side electrode and the first back-side electrode which is caused by the approach of the object to be detected; and a load sensor section that is disposed on a back side of the proximity sensor section, and that detects pressing and coordinates of the object to be detected, based on a load that is applied from the object to be detected via the proximity sensor section.

The state after the "approach" includes not only noncontact but also contact. The expression "made of an elastomer" includes not only the case where the object (the first base material, the first front-side electrodes, the first back-side electrodes, and the protective layer) is made of only the elastomer, but also the case where the object further contains a material other than the elastomer (e.g., a conductive filler in order to make the object conductive).

The hybrid sensor of the present invention includes the proximity sensor section and the load sensor section. The proximity sensor section can detect the approach of the object to be detected, based on a change in capacitance. The proximity sensor section can detect the coordinates of the object to be detected in a planar direction, based on coordinates of a location where the capacitance has changed. The load sensor section can detect pressing of the object to be detected. The hybrid sensor of the present invention can thus detect the approach, pressing, and coordinates of the object to be detected.

The proximity sensor section includes the protective layer, the first front-side electrodes, the first base material, and the first back-side electrodes from a front side (the load input side) toward a back side (any other layer may be interposed between adjoining ones of the layers). Each of the protective layer, the first front-side electrodes, the first base material, and the first back-side electrodes is made of an elastomer that is more elastic than resin. The proximity sensor section is therefore elastic. Accordingly, the proximity sensor section tends to be deformed by the load that is applied from the object to be detected. This makes it easier for the operator to tactually feel a stroke. Moreover, the elastic proximity sensor section is less likely to spread the load from the object to be detected in the planar direction. This increases detection accuracy of the coordinates in the planar direction.

The proximity sensor section of the hybrid sensor of the present invention may be used alone without being combined with the load sensor section.

(1-1) Preferably, in the configuration of (1), the proximity sensor section detects the approach and the coordinates of the object to be detected, based on an increase in the capacitance between the first front-side electrode and the first back-side electrode which is caused by the approach of the object to be detected. According to this configuration, a self-capacitance sensor can be used as the proximity sensor section.

(2) Preferably, in the configuration of (1), the proximity sensor section detects the approach and the coordinates of the object to be detected, based on a decrease in the capacitance between the first front-side electrode and the first back-side electrode which is caused as capacitance is generated between the first front-side electrode and the object to be detected by the approach of the object to be detected. According to this configuration, a mutual-capacitance sensor can be used as the proximity sensor section. This allows the hybrid sensor to be easily adapted to multi touch (simultaneous input at multiple points).

(3) Preferably, in the configuration of (1) or (2), the load sensor section includes a second base material having insulating properties and made of an elastomer, a plurality of second front-side electrodes disposed on a front side of the second base material, having conductive properties, and made of an elastomer, and a plurality of second back-side electrodes disposed on a back side of the second base material, having conductive properties, and made of an elastomer, and detects the pressing and the coordinates of the object to be detected, based on an increase in capacitance between the second front-side electrode and the second back-side electrode which is caused as an interelectrode distance between the second front-side electrode and the second back-side electrode is decreased by the load.

The load sensor section of the hybrid sensor having this configuration can detect the pressing (specifically, whether there is pressing or nor, the degree of pressing, whether there is a load or not, the level of load, the value of load, etc.) based on the change in capacitance. The load sensor section can detect the coordinates of the object to be detected in the planar direction, based on the coordinates of a location where the capacitance has changed.

The load sensor section includes the second front-side electrodes, the second base material, and the second back-side electrodes from the front side toward the back side (any other layer may be interposed between adjoining ones of the layers). Each of the second front-side electrodes, the second base material, and the second back-side electrodes is made of an elastomer that is more elastic than resin. The load sensor section is therefore elastic. Accordingly, the load sensor section tends to be deformed by the load that is applied from the object to be detected. This makes it easier for the operator to tactually feel a stroke. Moreover, the elastic load sensor section is less likely to spread the load from the object to be detected in the planar direction. This increases detection accuracy of the coordinates in the planar direction.

(4) Preferably, in the configuration of (3), the hybrid sensor further includes: an intermediate layer disposed between the proximity sensor section and the load sensor section, having conductive properties, and being elastic and grounded.

According to this configuration, the intermediate layer is interposed between the proximity sensor section and the load sensor section. The intermediate layer has conductive properties, and is grounded. The proximity sensor section and the load sensor section are therefore less likely to be adversely affected by each other's noise. This increases detection accuracy of the proximity sensor section and the load sensor section.

(5) Preferably, in the configuration of (4), an insulating spacer having insulating properties and made of an elastomer is disposed on at least one of front and back sides of the intermediate layer.

This configuration can increase the distance (interelectrode distance) in the front-back direction between the first back-side electrode of the proximity sensor section and the second front-side electrode of the load sensor section. This can suppress generation of stray capacitance between the first back-side electrode and the second front-side electrode, and can reduce mutual interference between the proximity sensor section and the load sensor section, thereby increasing detection accuracy.

(6) Preferably, in the configuration of (5), the insulating spacer has a load spread suppressing mechanism that suppresses spreading of the load in the planar direction. In order to suppress generation of stray capacitance between the first back-side electrode and the second front-side electrode, it is more preferable for the insulating spacer to have a larger thickness in the front-back direction. However, if the thickness in the front-back direction of the insulating spacer is increased, the load applied from the object to be detected is more likely to be spread in the planar direction (specifically, the direction perpendicular to the front-back direction of the insulating spacer, the direction in which the front or back surface of the insulating spacer extends) when it is transmitted in the insulating spacer. This reduces detection accuracy of the coordinates in the planar direction in the load sensor located on the back side of the insulating spacer.

Since the insulating spacer in the above configuration has the load spread suppressing mechanism, the load applied from the object to be detected is less likely to be spread in the planar direction when it is transmitted in the insulating spacer. This increases detection accuracy of the coordinates in the planar direction, and increases detection accuracy of the load.

(7) Preferably, in the configuration of (6), the load sensor section has a plurality of overlapping portions where the plurality of second front-side electrodes overlap the plurality of second back-side electrodes as viewed from a front side or a back side, and the load spread suppressing mechanism is interposed between the overlapping portions that adjoin each other in the planar direction, as viewed from the front side or the back side.

It is herein assumed that a load is input from the front side of any one of the plurality of overlapping portions (i.e., load detecting portions) adjoining each other in the planar direction, via the insulating spacer. According to this configuration, the load spread suppressing mechanism is interposed between any one of the overlapping portions and the overlapping portion adjoining this overlapping portion. The load is therefore less likely to spread in the planar direction in the insulating spacer. This can suppress erroneous transmission of the input load to the overlapping portion adjoining the any one of the overlapping portions.

(8) Preferably, in the configuration of (6) or (7), the load spread suppressing mechanism is a load spread suppressing groove that is formed in a front or back surface of the insulating spacer.

The insulating spacer is thinner in the front-back direction in the region where the load spread suppressing groove is formed than in the region where the load spread suppressing groove is not formed. This reduces a spring constant in the planar direction, and can therefore suppress spreading of the load in the planar direction.

(9) Preferably, in the configuration of (6) or (7), the load spread suppressing mechanism is a load spread suppressing hole that extends through the insulating spacer in the front-back direction.

The insulating spacer has a smaller spring constant in the planar direction in the region where the load spread suppressing hole is formed than in the region where the load spread suppressing hole is not formed. This can suppress spreading of the load in the planar direction.

(10) Preferably, in the configuration of any one of (3) to (9), the proximity sensor section includes a first front-side insulating layer disposed on the front side of the plurality of first front-side electrodes and made of an elastomer, and a first back-side insulating layer disposed on a back side of the plurality of first back-side electrodes and made of an elastomer, the load sensor section includes a second front-side insulating layer disposed on a front side of the plurality of second front-side electrodes and made of an elastomer, and a second back-side insulating layer disposed on a back side of the plurality of second back-side electrodes and made of an elastomer, and the hybrid sensor satisfies at least one of the following (a) and (b): (a) in the proximity sensor section, the first front-side electrodes are printed on at least one of the first base material and the first front-side insulating layer, and the first back-side electrodes are printed on at least one of the first base material and the first back-side insulating layer; and (b) in the load sensor section, the second front-side electrodes are printed on at least one of the second base material and the second front-side insulating layer, and the second back-side electrodes are printed on at least one of the second base material and the second back-side insulating layer.

This configuration facilitates formation of the first front-side electrodes, the first back-side electrodes, the second front-side electrodes, and the second back-side electrodes. Moreover, this configuration allows these electrodes to be formed and arranged at the same time, increasing design flexibility of the shape of the electrodes and increasing shape accuracy of the electrodes. In the case of (a), relative positioning between the first front-side electrodes and the first back-side electrodes is facilitated. In the case of (b), relative positioning between the second front-side electrodes and the second back-side electrodes is similarly facilitated.

(11) Preferably, in the configuration of any one of (1) to (10), at least one of a protruding portion and a recessed portion is disposed on a surface of the protective layer. This configuration allows the operator to determine the position on the hybrid sensor the object to be detected is to be made to approach, the position on the hybrid sensor against which the object to be detected is to be pressed, a path along which the object to be detected is to be slid on the hybrid sensor, etc. with respect to the protruding portion or the recessed portion. The operator can thus operate the hybrid sensor mainly tactually.

Effects of the Invention

According to the present invention, a hybrid sensor can be provided which is capable of detecting the approach, pressing, and coordinates of an object to be detected, which makes it more likely for the operator to tactually feel a stroke, and which has high coordinate detection accuracy.

BRIEF DESCRIPTION OF THE DRAWINGS

FIG. 5 is a block diagram of the hybrid sensor.
FIG. 6A is an enlarged view of a portion in a box VI in FIG. 4 in the state where a finger is not approaching.

DESCRIPTION OF THE REFERENCE NUMERALS

1: Hybrid Sensor, 2: Proximity Sensor Section, 3: Load Sensor Section, 4: Intermediate Layer, 6: Sensor Stack, 7: Control Unit, 9: Finger (Object to be Detected)
20: First Base Material, 21: Protective Layer, 22: First Front-Side Insulating Layer, 23: First Back-Side Insulating Layer (Insulating Spacer), 25: Insulating Spacer, 30: Second Base Material, 32: Second Front-Side Insulating Layer (Insulating Spacer), 33: Second Back-Side Insulating Layer, 34: Underlying Layer, 35: Insulating Spacer, 70: Control Section, 71: Transmitting Section, 72: Receiving Section, 73: Computer, 74: Transmitting-Side Coupling Section, 75: Receiving-Side Coupling Section
210: Protruding Portion, 250: Load Spread Suppressing Groove, 251: Load Spread Suppressing Hole, 350: Load Spread Suppressing Groove, 351: Load Spread Suppressing Hole, 700: DSP, 701: SRAM, 710: DAC, 711: DDS, 712: Multiplexer, 713: Operational Amplifier, 720: ADC, 721: Low Pass Filter, 722: Multiplexer, 723: Operational Amplifier, 740a to 740d: Switch, 750a to 750d: Switch
A: Overlapping Portion, B: Electric Field, Ca: Capacitance, Cb: Capacitance, F: Load, P: Axis, X1 to X8: First Front-Side Electrode, X1a: Wide Portion, X1b: Narrow Portion, Y1 to Y8: First Back-Side Electrode, d: Interelectrode Distance, th1: Small Load Threshold, th2: Large Load Threshold, th3: Approach Threshold, x1 to x8: Second Front-Side Electrode, y1 to y8: Second Back-Side Electrode

MODES FOR CARRYING OUT THE INVENTION

Embodiments of a hybrid sensor according to the present invention will be described below.

First Embodiment

Configuration of Hybrid Sensor

Figure 1:
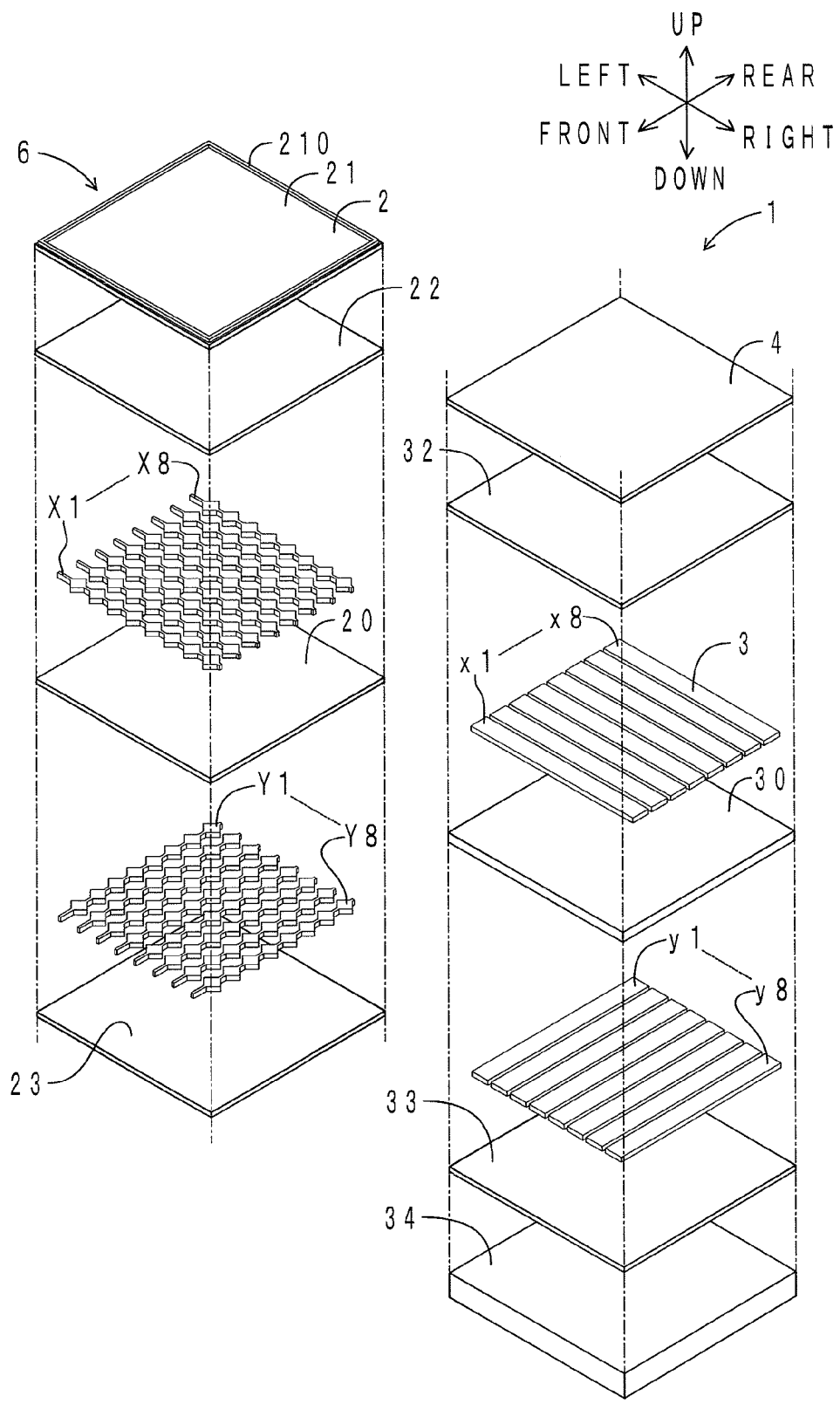
FIG. 1 is an exploded perspective view of a hybrid sensor according to a first embodiment.
Figure 2:
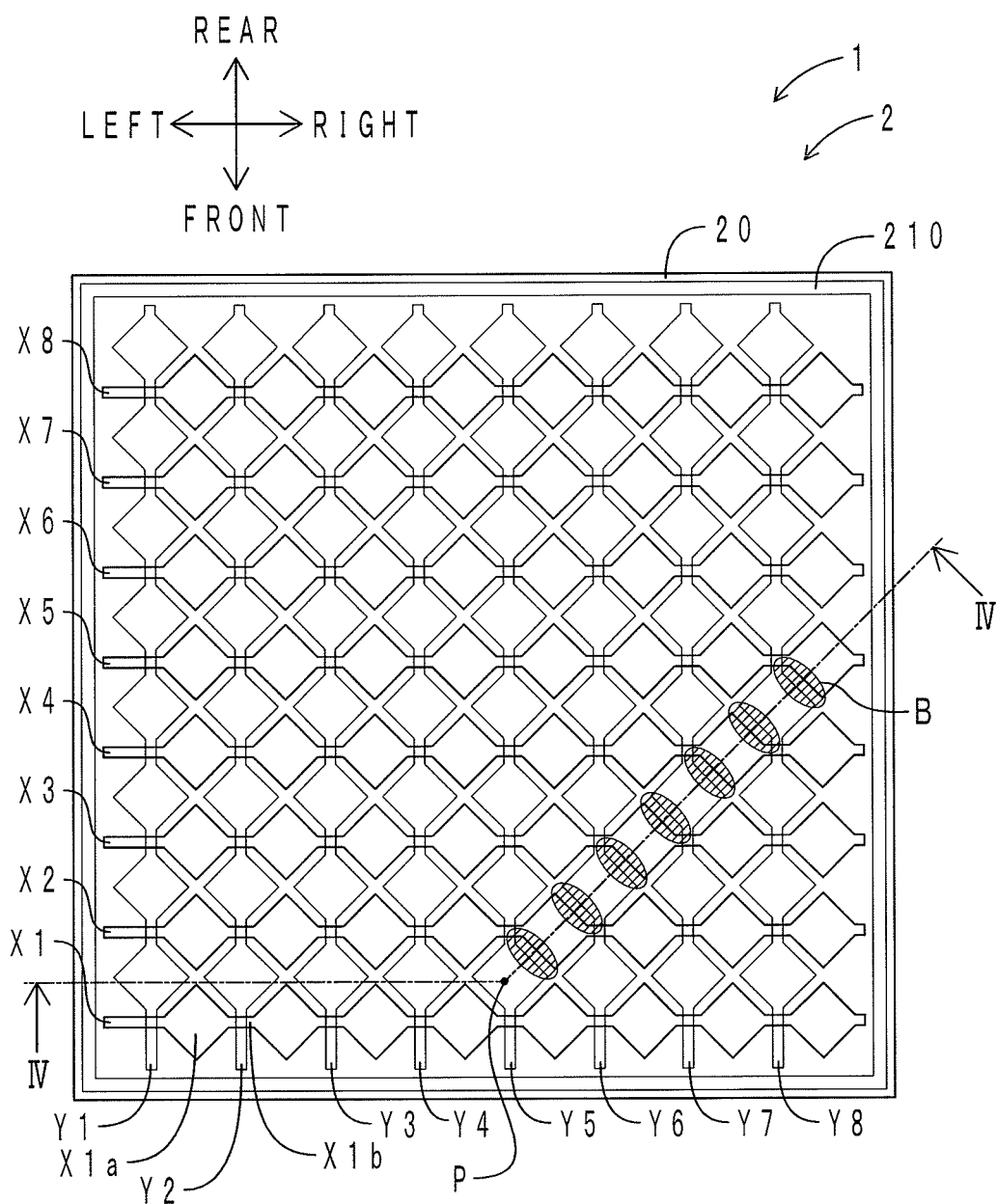
FIG. 2 is a transparent top view of a proximity sensor section of the hybrid sensor.
Figure 3:
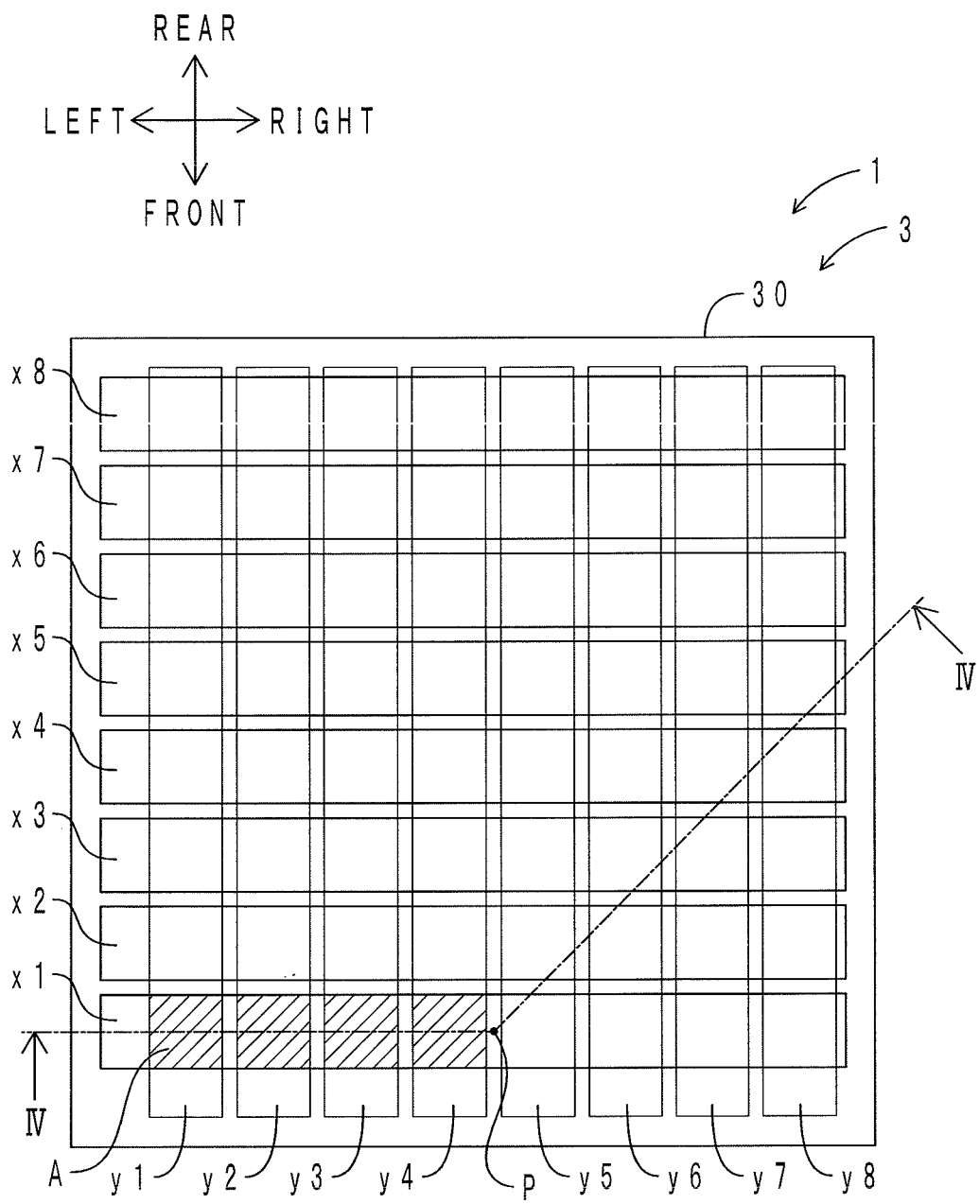
FIG. 3 is a transparent top view of a load sensor section of the hybrid sensor.
Figure 4:
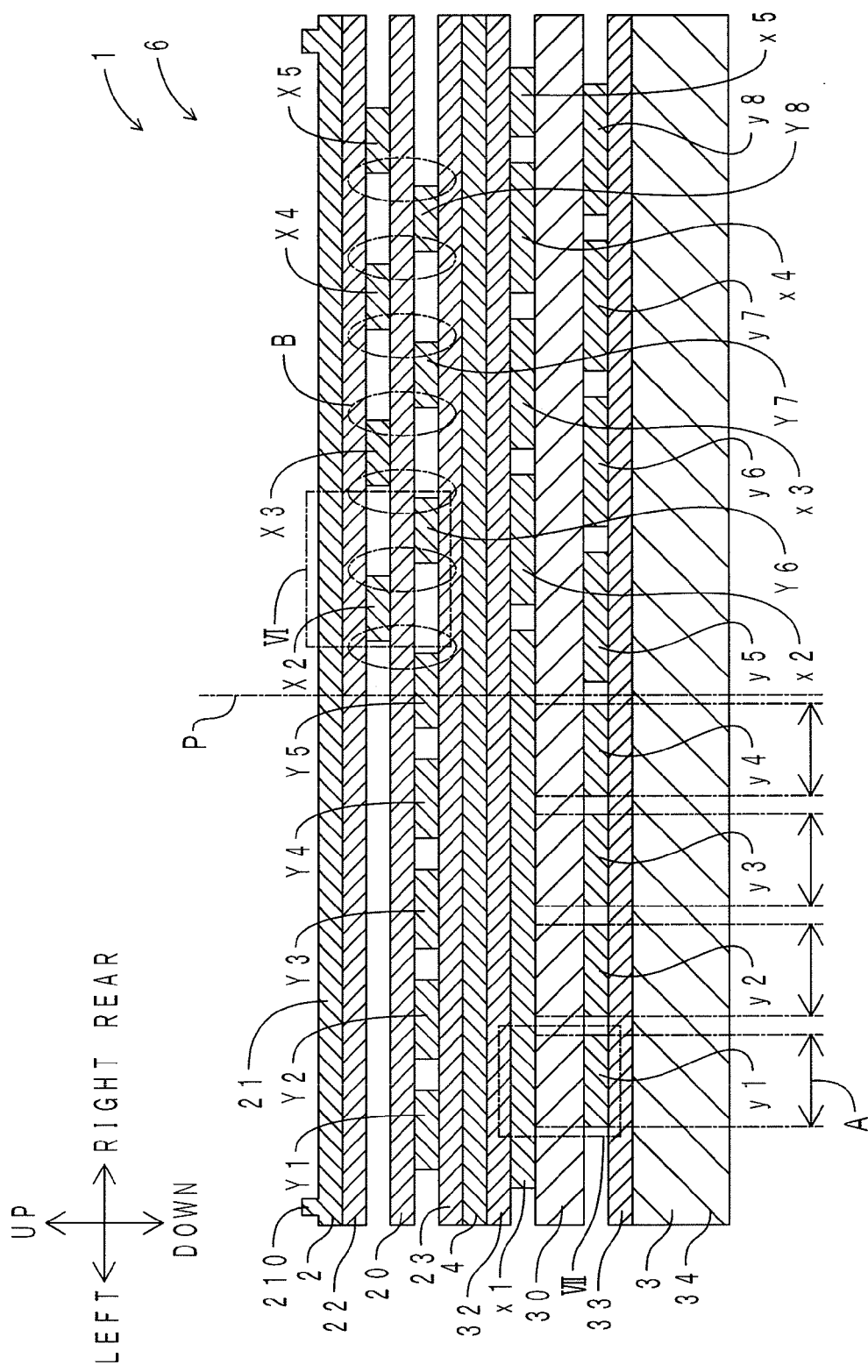
FIG. 4 is a sectional view taken along a direction IV-IV passing an axis P in FIGS. 2 and 3.

First, the configuration of a hybrid sensor of the present embodiment will be described. FIG. 1 is an exploded perspective view of the hybrid sensor of the present embodiment. FIG. 2 is a transparent top view of a proximity sensor section of the hybrid sensor. FIG. 3 is a transparent top view of a load sensor section of the hybrid sensor. FIG. 4 is a sectional view taken along a direction VI-VI passing through an axis P in FIGS. 2 and 3. FIG. 5 is a block diagram of the hybrid sensor. As shown in FIGS. 1 to 5, a hybrid sensor 1 of the present embodiment includes a sensor stack 6 and a control unit 7.

{Sensor Stack 6}

The sensor stack 6 includes a proximity sensor section 2, a load sensor section 3, and an intermediate layer 4.

(Proximity Sensor Section 2)

The proximity sensor section 2 is formed by stacking a protective layer 21, a first front-side insulating layer 22, eight first front-side electrodes X1 to X8, a first base material 20, eight first back-side electrodes Y1 to Y8, and a first back-side insulating layer 23 from top (front) to bottom (back). The first back-side insulating layer 23 is included in a concept of the "insulating spacer" of the present invention.

The first base material 20 is made of urethane rubber, and is in the form of a square sheet. The first base material 20 is elastic and has insulating properties.

Each of the eight first front-side electrodes X1 to X8 has a strip shape that is long in the left-right direction. The eight first front-side electrodes X1 to X8 are arranged side by side in the front-rear direction on the upper surface (front surface) of the first base material 20 so as to be parallel to each other. Each of the eight first front-side electrodes X1 to X8 contains acrylic rubber and conductive carbon black. The first base material 20 has the eight first front-side electrodes X1 to X8 screen printed on its upper surface. Each of the eight first front-side electrodes X1 to X8 is elastic and conductive.

As shown in FIG. 2, wide portions X1a having a great width in the front-rear direction and narrow portions X1b having a small width in the front-rear direction are alternately arranged side by side in the first front-side electrode X1. The wide portions X1a have a diamond shape, and the narrow portions X1b have a rectangular shape. Wide portions and narrow portions are arranged in the first front-side electrodes X2 to X8 in a manner similar to that in the first front-side electrode X1.

Each of the eight first back-side electrodes Y1 to Y8 has a strip shape that is long in the front-rear direction. The eight first back-side electrodes Y1 to Y8 are arranged side by side in the left-right direction on the lower surface (back surface) of the first base material 20 so as to be parallel to each other. The configuration of the eight first back-side electrodes Y1 to Y8 and the way they are arranged on the lower surface of the first base material 20 are similar to the configuration of the eight first front-side electrodes X1 to X8 and the way they are arranged on the upper surface on the first base material 20. The wide portions of the first front-side electrodes X1 to X8 and the wide portions of the first back-side electrodes Y1 to Y8 are located side by side in a horizontal direction (planar direction) as viewed from above or below. An electric field B is generated between adjoining ones of the wide portions.

The first front-side insulating layer 22 is made of acrylic rubber, and is in the form of a square sheet. The first front-side insulating layer 22 is elastic and has insulating properties. The first front-side insulating layer 22 is disposed above the eight first front-side electrodes X1 to X8.

The protective layer 21 is made of silicone rubber, and is in the form of a square sheet. The protective layer 21 is elastic and has insulating properties. The protective layer 21 is disposed above the first front-side insulating layer 22. A protruding portion 210 is disposed on the upper surface of the protective layer 21. The protruding portion 210 is in the form of a square frame. The protruding portion 210 has such a height that a finger (object to be detected) described below can tactually feel it. Various commands are input from the operator to the sensor stack 6 via the protective layer 21.

The first back-side insulating layer 23 is made of acrylic rubber, and is in the form of a square sheet. The first back-side insulating layer 23 is elastic and has insulating properties. The first back-side insulating layer 23 is disposed below the eight back-side electrodes Y1 to Y8.

(Intermediate Layer 4)

The intermediate layer 4 is made of a polyester fiber fabric having its outer surface coated with a metal, and is in the form of a square fabric. The intermediate layer 4 is elastic and conductive. The intermediate layer 4 is disposed below the proximity sensor section 2. The intermediate layer 4 is earthed (grounded).

(Load Sensor Section 3)

The load sensor section 3 is formed by stacking a second front-side insulating layer 32, eight second front-side electrodes x1 to x8, a second base material 30, eight second back-side electrodes y1 to y8, a second back-side insulating layer 33, and an underlying layer 34 from top (front) to bottom (back). The second front-side insulating layer 32 is included in a concept of the "insulating spacer" of the present invention.

The second base material 30 is made of urethane rubber, and is in the form of a square sheet. The second base material 30 is elastic and has insulating properties.

Each of the eight second front-side electrodes x1 to x8 has a strip shape that is long in the left-right direction. The eight second front-side electrodes x1 to x8 are arranged side by side in the front-rear direction on the upper surface of the second base material 30 so as to be parallel to each other. Each of the eight second front-side electrodes x1 to x8 contains acrylic rubber and conductive carbon black. The second base material 30 has the eight second front-side electrodes x1 to x8 screen printed on its upper surface. Each of the eight second front-side electrodes x1 to x8 is elastic and conductive.

Each of the eight second back-side electrodes y1 to y8 has a strip shape that is long in the front-rear direction. The eight second back-side electrodes y1 to y8 are arranged side by side in the left-right direction on the lower surface of the second base material 30 so as to be parallel to each other. The configuration of the eight second back-side electrodes y1 to y8 and the way they are arranged on the lower surface of the second base material 30 are similar to the configuration of the eight second front-side electrodes x1 to x8 and the way they are arranged on the upper surface on the second base material 30. The second front-side electrodes x1 to x8 overlap the second back-side electrodes y1 to y8 in the top-bottom direction (front-back direction, load transmission direction) as viewed from above or below. That is, overlapping portions A are formed between the second front-side electrodes x1 to x8 and the second back-side electrodes y1 to y8.

The second front-side insulating layer 32 is made of acrylic rubber, and is in the form of a square sheet. The second front-side insulating layer 32 is elastic and has insulating properties. The second front-side insulating layer 32 is disposed between the intermediate layer 4 and the eight second front-side electrodes x1 to x8.

The second back-side insulating layer 33 is made of acrylic rubber, and is in the form of a square sheet. The second back-side insulating layer 33 is elastic and has insulating properties. The second back-side insulating layer 33 is disposed below the eight second back-side electrodes y1 to y8.

The underlying layer 34 is made of polyurethane foam, and is in the form of a square plate. The underlying layer 34 is elastic and has insulating properties. The underlying layer 34 is disposed below the second back-side insulating layer 33.

{Control Unit 7}

As shown in FIG. 5, the control unit 7 includes a control section 70, a transmitting section 71, a receiving section 72, and a computer 73.

(Control Section 70)

The control section 70 includes a digital signal processor (DSP) 700 and a static random access memory (SRAM) 701. The DSP 700 is used as a microcomputer (computing section). The SRAM 701 is used as a memory section. Thresholds for determining the approach, a small load, and a large load (an approach threshold, a small load threshold, a large load threshold) are stored in the SRAM 701. A map for evaluating coordinates of a finger (object to be detected) in the horizontal direction (positions in the left-right direction and the front-rear directions) in the proximity sensor section 2 and coordinates of the finger in the horizontal direction in the load sensor section 3 by a common coordinate system is also stored in the SRAM 701. The SRAM 701 is electrically connected to the DSP 700.

(Transmitting Section 71)

The transmitting section 71 includes a digital-to-analog converter (DAC) 710, a direct digital synthesizer (DDS) 711, four multiplexers 712, and eight operational amplifiers 713.

The DAC 710 converts a digital signal to an analog signal. The DAC 710 is electrically connected to the DSP 700. The DDS 711 is used as a sinusoidal oscillator. The DDS 711 is electrically connected to the DAC 710. Each of the four analog multiplexers 712 is electrically connected to the DDS 711. The four multiplexers 712 output a sinusoidal current to the eight operational amplifiers 713 in a scanning manner by sequential switching. Each of the eight operational amplifiers 713 converts the current received from the multiplexer 712 to a voltage. That is, each of the eight operational amplifiers 713 is used as a current-to-voltage converter. The eight operational amplifiers 713 are electrically connected to the eight first front-side electrodes X1 to X8.

(Receiving Section 72)

The receiving section 72 includes four analog-to-digital converters (ADCs) 720, four low pass filters 721, four multiplexers 722, and eight operational amplifiers 723.

The eight operational amplifiers 723 are electrically connected to the eight first back-side electrodes Y1 to Y8. Each of the eight operational amplifiers 723 is used as a current-to-voltage converter. The four analog multiplexers 722 are electrically connected to the eight operational amplifiers 723. The four multiplexers 722 are connected to the eight operational amplifiers 723 by sequential switching. Each of the four low pass filters 721 removes high frequency components of a voltage. The four low pass filters 721 are electrically connected to the four multiplexers 722. The four ADCs 720 convert an analog signal to a digital signal. The four ADCs 720 are electrically connected to the four low pass filters 721. The four ADCs 720 are electrically connected to the DSP 700.

(Computer 73)

The computer 73 is electrically connected to the DSP 700. The computer 73 sends a command according to operation of the operator (approach, sliding, small load input, large load input, etc.) to an actuator (not shown).

The control unit 7 is electrically connected also to the load sensor section 3 shown in FIG. 3, similarly to the proximity sensor section 2 shown in FIG. 5. That is, a voltage is sequentially supplied to the second front-side electrodes x1 to x8 of the load sensor section 3 via the multiplexers. A current is output from the second back-side electrodes y1 to y8.

Operation of Proximity Sensor Section 2 of Hybrid Sensor 1

Figure 6B:
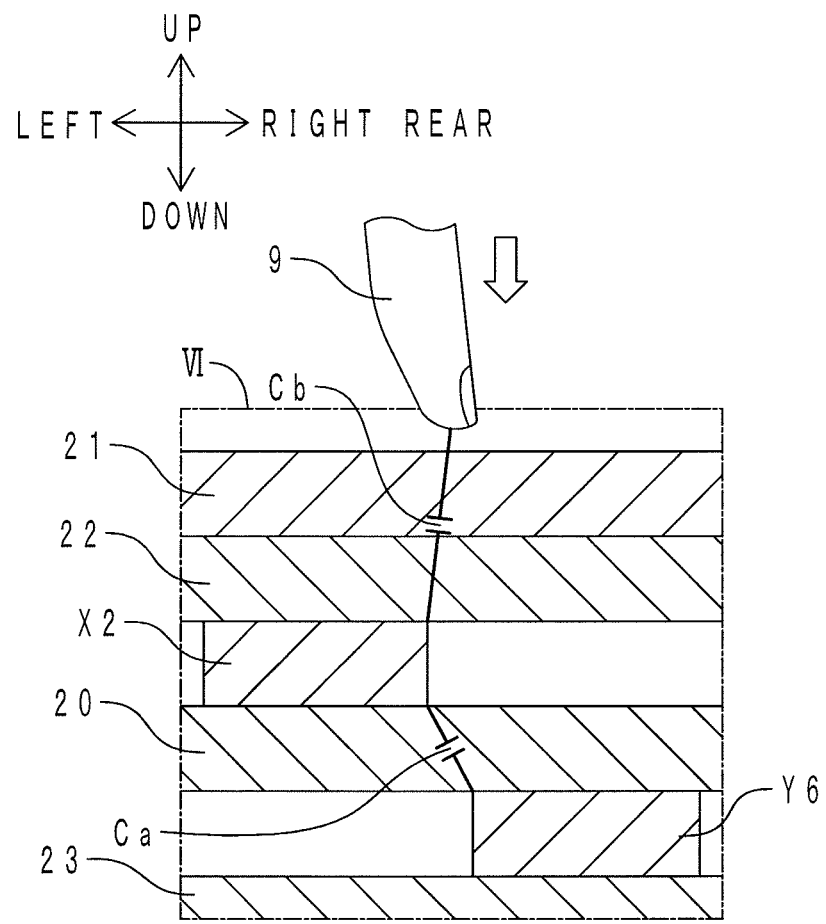
FIG. 6B is an enlarged view of the portion in the box VI in FIG. 4 in the state where a finger is approaching.

Operation of the proximity sensor section 2 of the hybrid sensor 1 of the present embodiment will be described below. FIG. 6A is an enlarged view of a portion in a box VI in FIG. 4 in the state where a finger is not approaching. FIG. 6B is an enlarged view of the portion in the box VI in FIG. 4 in the state where a finger is approaching. As shown in FIG. 6A, capacitance Ca is generated between the first front-side electrode X2 and the first back-side electrode Y6 by a voltage that is supplied from the transmitting section 71 shown in FIG. 5.

As shown in FIG. 6B, as a finger (object to be detected, which is conductive and is earthed via a human body) 9 approaches the protective layer 21, capacitance Cb is generated between the first front-side electrode X2 and the finger 9. A current that is input to the operational amplifier 723 shown in FIG. 5 is therefore smaller in the state where the finger 9 is approaching (FIG. 6B) than in the state where the finger 9 is not approaching (FIG. 6A). The DSP 700 calculates the amount of change in capacitance between the first front-side electrode X2 and the first back-side electrode Y6 based on this change in current.

Operation of Load Sensor Section 3 of Hybrid Sensor 1

Figure 7A:
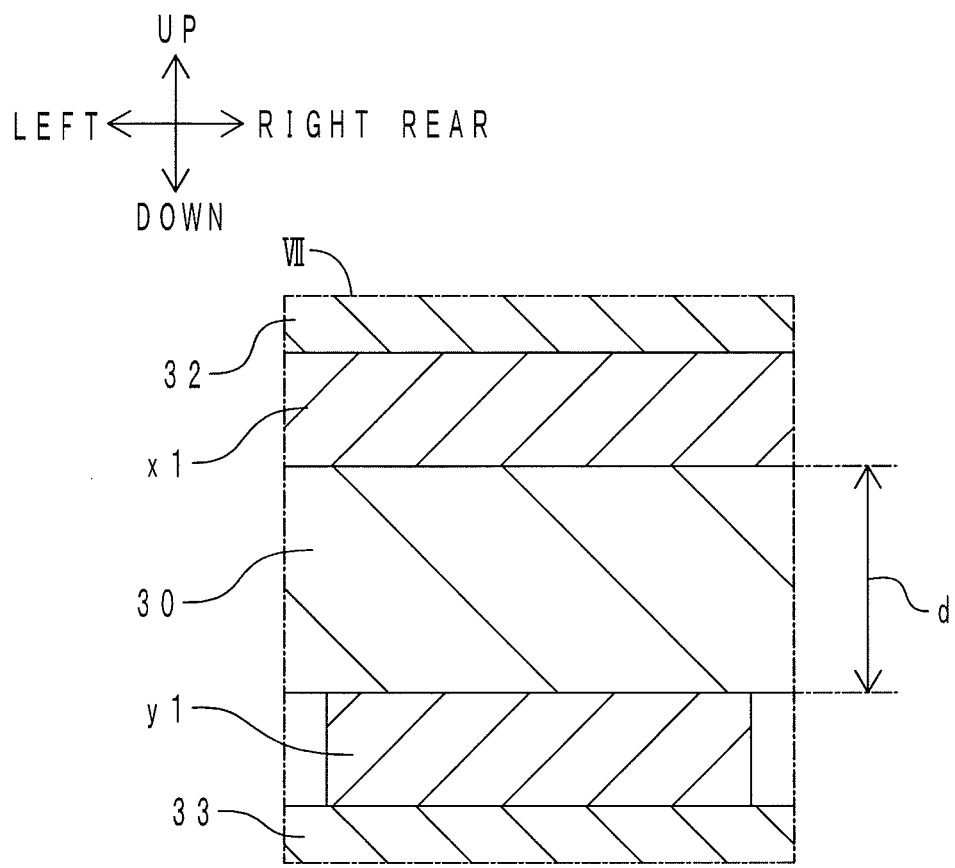
FIG. 7A is an enlarged view of a portion in a box VII in FIG. 4 in the state where a finger is not being pressed against the hybrid sensor.
Figure 7B:
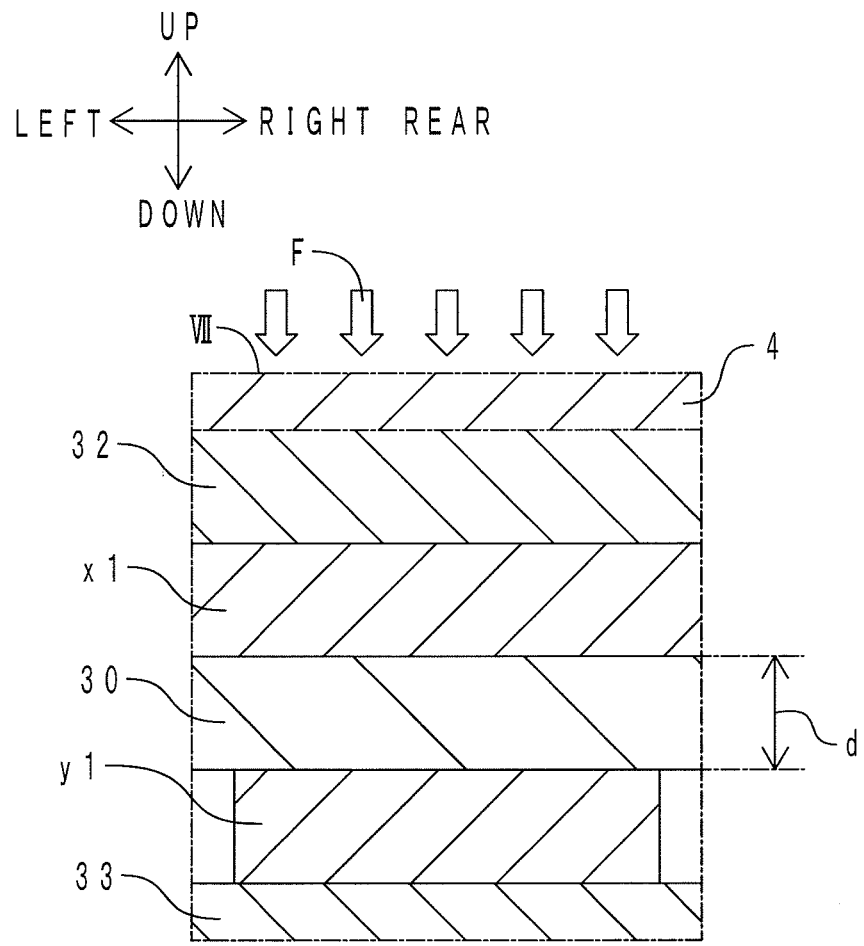
FIG. 7B is an enlarged view of the portion in the box VII in FIG. 4 in the state where a finger is being pressed against the hybrid sensor.

Operation of the load sensor section 3 of the hybrid sensor 1 of the present embodiment will be described below. FIG. 7A is an enlarged view of a portion in a box VII in FIG. 4 in the state where a finger is not being pressed against the hybrid sensor 1. FIG. 7B is an enlarged view of the portion in the box VII in FIG. 4 in the state where a finger is being pressed against the hybrid sensor 1. As shown in FIG. 7A, no load is applied to the second base material 30 as a dielectric layer in the state where a finger is not being pressed against the hybrid sensor 1. The thickness in the top-bottom direction of the second base material 30 corresponds to the interelectrode distance "d" between the second front-side electrode x1 and the second back-side electrode y1.

As shown in FIG. 4, all of the members of the proximity sensor section 2 and the intermediate layer 4 are elastic. Accordingly, as the finger 9 is pressed against the hybrid sensor 1, the members of the proximity sensor section 2 and the intermediate layer 4 are locally depressed downward in a region pressed with the finger 9. That is, the proximity sensor section 2 and the intermediate layer 4 are not entirely depressed downward.

As shown in FIG. 7B, as the finger 9 is pressed against the hybrid sensor 1, the second base material 30 is locally compressed by a load F applied from above. This reduces the interelectrode distance "d" between the second front-side electrode x1 and the second back-side electrode y1. The DSP 700 calculates the amount of change in capacitance between the second front-side electrode x1 and the second back-side electrode y1 based on this change in interelectrode distance d.

Method for Determining Approach, Small Load, and Large Load in the Hybrid Sensor 1

Figure 8:
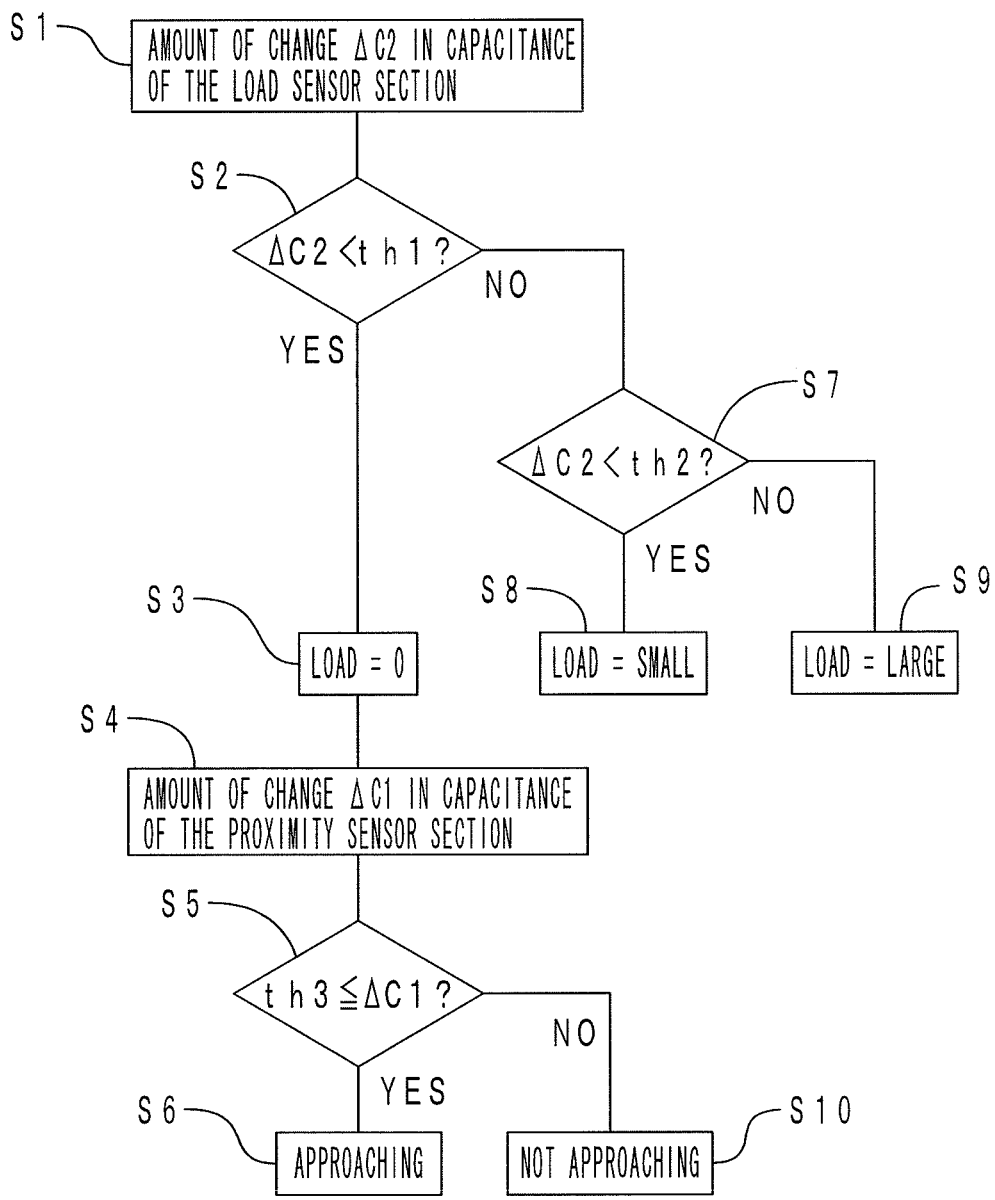
FIG. 8 is a flowchart of a routine that is executed by a control unit of the hybrid sensor.

A method for determining the approach, a small load, and a large load in the hybrid sensor 1 of the present embodiment will be described below. FIG. 8 is a flowchart of a routine that is executed by the control unit of the hybrid sensor of the present embodiment.

As shown in FIG. 5, the control unit 7 monitors the capacitance of the proximity sensor section 2 and the capacitance of the load sensor section 3 at predetermined sampling intervals. That is, the DSP 700 shown in FIG. 5 compares an amount of change $\Delta C2$ in capacitance of the load sensor section 3 with a small load threshold th1 stored in the SRAM 701 at the predetermined sampling intervals (S1, S2 in FIG. 8).

If the comparison (hereinafter referred to as the "first comparison") shows that the amount of change $\Delta C2$ is smaller than the small load threshold th1, the DSP 700 determines that no load is being applied to the load sensor section 3 (S3 in FIG. 8). In this case, the DSP 700 shown in FIG. 5 compares an amount of change $\Delta C1$ in capacitance of the proximity sensor section 2 with an approach threshold th3 stored in the SRAM 701 (S4, S5 in FIG. 8).

If the comparison (hereinafter referred to as the "second comparison") shows that the amount of change $\Delta C1$ is equal to or larger than the approach threshold th3, the DSP 700 determines that the finger 9 is approaching (including contact) the proximity sensor section 2 (S6 in FIG. 8). The DSP 700 also specifies the coordinates of the location the finger 9 is approaching. The DSP 700 transmits information on the approach of the finger 9 and the coordinates thereof to the computer 73. The computer 73 sends a command corresponding to the information received from the DSP 700 to the actuator. If the second comparison shows that the amount of change $\Delta C1$ is less than the approach threshold th3, the DSP 700 determines that the finger 9 is not approaching the proximity sensor section 2 (S10 in FIG. 8).

If the first comparison (S2 in FIG. 8) shows that the amount of change $\Delta C2$ is equal to or larger than the small load threshold th1, the DSP 700 shown in FIG. 5 compares the amount of change $\Delta C2$ with a large load threshold th2 stored in the SRAM 701 (S7 in FIG. 8).

If the comparison (hereinafter referred to as the "third comparison") shows that the amount of change $\Delta C2$ is smaller than the large load threshold th2, the DSP 700 determines that a small load is being applied by the finger 9 (S8 in FIG. 8). The DSP 700 also specifies the coordinates of the pressed finger 9. The DSP 700 transmits information on the small load of the finger 9 and the coordinates thereof to the computer 73. The computer 73 sends a command corresponding to the information received from the DSP 700 to the actuator. If the third comparison shows that the amount of change $\Delta C2$ is equal to or larger than the large load threshold th2, the DSP 700 determines that a large load is being applied by the finger 9 (S9 in FIG. 8). The DSP 700 also specifies the coordinates of the pressed finger 9. The DSP 700 transmits information on the large load of the finger 9 and the coordinates thereof to the computer 73. The computer 73 sends a command corresponding to the information received from the DSP 700 to the actuator.

As described above, the hybrid sensor 1 of the present embodiment can determine "the fact that the finger 9 is separated from the hybrid sensor 1," "the fact that the finger 9 is approaching the hybrid sensor 1, and the approach coordinates," "the fact that a small load is being applied from the finger 9 to the hybrid sensor 1, and the coordinates of the portion being subjected to the load," and "the fact that a large load is being applied from the finger 9 to the hybrid sensor 1, and the coordinates of the portion being subjected to the load," according to the state of the finger 9 with respect to the hybrid sensor 1.

Functions and Effects

The functions and effects of the hybrid sensor 1 of the present embodiment will be described below. The hybrid sensor 1 of the present embodiment includes the proximity sensor section 2 and the load sensor section 3. The proximity sensor section 2 can detect the approach of the finger 9 based on a change in capacitance. The proximity sensor section 2 can also detect the coordinates of the finger 9 in the planar direction based on the coordinates of a location where the capacitance has changed. The load sensor section 3 can detect pressing of the finger 9. The hybrid sensor 1 of the present embodiment can thus detect the approach, pressing, and coordinates of the finger 9.

Each of the protective layer 21, the first front-side insulating layer 22, the first front-side electrodes X1 to X8, the first base material 20, the first back-side electrodes Y1 to Y8, and the first back-side insulating layer 23 in the proximity sensor section 2 is made of an elastomer that is more elastic than resin. The proximity sensor section 2 is therefore elastic. Accordingly, the proximity sensor section 2 tends to be deformed by the load from the finger 9. This makes it easier for the operator to tactually feel a stroke. The elastic proximity sensor section 2 is less likely to spread the load from the finger 9 in the planar direction. This results in high detection accuracy of the coordinates in the planar direction. The proximity sensor section 2 may not be combined with the load sensor section 3, and may be used alone.

The load sensor section 3 of the hybrid sensor 1 of the present embodiment can detect the level of the load (small load, large load) based on a change in capacitance. The load sensor section 3 can also detect the coordinates of the finger 9 in the planar direction based on the coordinates of a location where the capacitance has changed.

Each of the second front-side insulating layer 32, the second front-side electrodes x1 to x8, the second base material 30, the second back-side electrodes y1 to y8, and the second back-side insulating layer 33 in the load sensor section 3 is made of an elastomer that is more elastic than resin. The load sensor section 3 is therefore elastic. Accordingly, the load sensor section 3 tends to be deformed by the load from the finger 9. This makes it easier for the operator to tactually feel a stroke. The elastic load sensor section 3 is less likely to spread the load from the finger 9 in the planar direction. This results in high detection accuracy of the coordinates in the planar direction.

The intermediate layer 4 of the hybrid sensor 1 of the present embodiment is conductive. The intermediate layer 4 is earthed. The proximity sensor section 2 and the load sensor section 3 are therefore less likely to be adversely affected by each other's noise. This increases detection accuracy of the proximity sensor section 2 and the load sensor section 3.

The intermediate layer 4 is made of a fabric (woven fabric) that is more elastic than resin (e.g., has a smaller Young's modulus than resin or has a smaller spring constant in the top-bottom direction and the horizontal direction than the intermediate layer 4 made of resin). Since the fabric (woven fabric) is structurally stretchable, the intermediate layer 4 can be stretched and deformed by the load from the finger 9. This makes it easier for the operator to tactually feel a stroke. The elastic intermediate layer 4 is less likely to spread the load from the finger 9 in the planar direction. Detection accuracy of the coordinates in the planar direction is therefore high.

The first back-side insulating layer 23 and the second front-side insulating layer 32 are disposed on the upper and lower sides of the intermediate layer 4. This can increase the distance (interelectrode distance) in the top-bottom direction between the first back-side electrodes Y1 to Y8 of the proximity sensor section 2 and the second front-side electrodes x1 to x8 of the load sensor section 3. This can suppress generation of stray capacitance between the first back-side electrodes Y1 to Y8 and the second front-side electrodes x1 to x8, and can reduce mutual interference between the proximity sensor section 2 and the load sensor section 3, thereby increasing detection accuracy of the proximity sensor section 2 and the load sensor section 3.

The protective layer 21 of the proximity sensor section 2 has the protruding portion 210. This allows the operator to determine the position on the hybrid sensor 1 the finger 9 is to be made to approach, the position on the hybrid sensor 1 against which the finger 9 is to be pressed, a path along which the finger 9 is to be slid on the hybrid sensor 1, etc. with respect to the protruding portion 210 without visually checking these positions. This makes it easier for the operator to tactually operate the hybrid sensor 1. Since the protective layer 21 is made of an elastomer, the protruding portion 210 can be easily formed on the protective layer 21 by injection molding etc.

The underlying layer 34 of the load sensor section 3 is made of a foam material that is more elastic than resin. The underlying layer 34 therefore tends to be deformed by the load from the finger 9. This makes it easier for the operator to tactually feel a stroke.

Both the proximity sensor section 2 and the load sensor section 3 can be adapted to multi touch (simultaneous input at multiple points). This allows for numerous variations of commands that can be used by the operator.

Second Embodiment

A hybrid sensor of the present embodiment is different from that of the first embodiment in that a control unit includes a transmitting-side coupling section and a receiving-side coupling section. Only the difference between the first and second embodiment will be described below.

Figure 9:
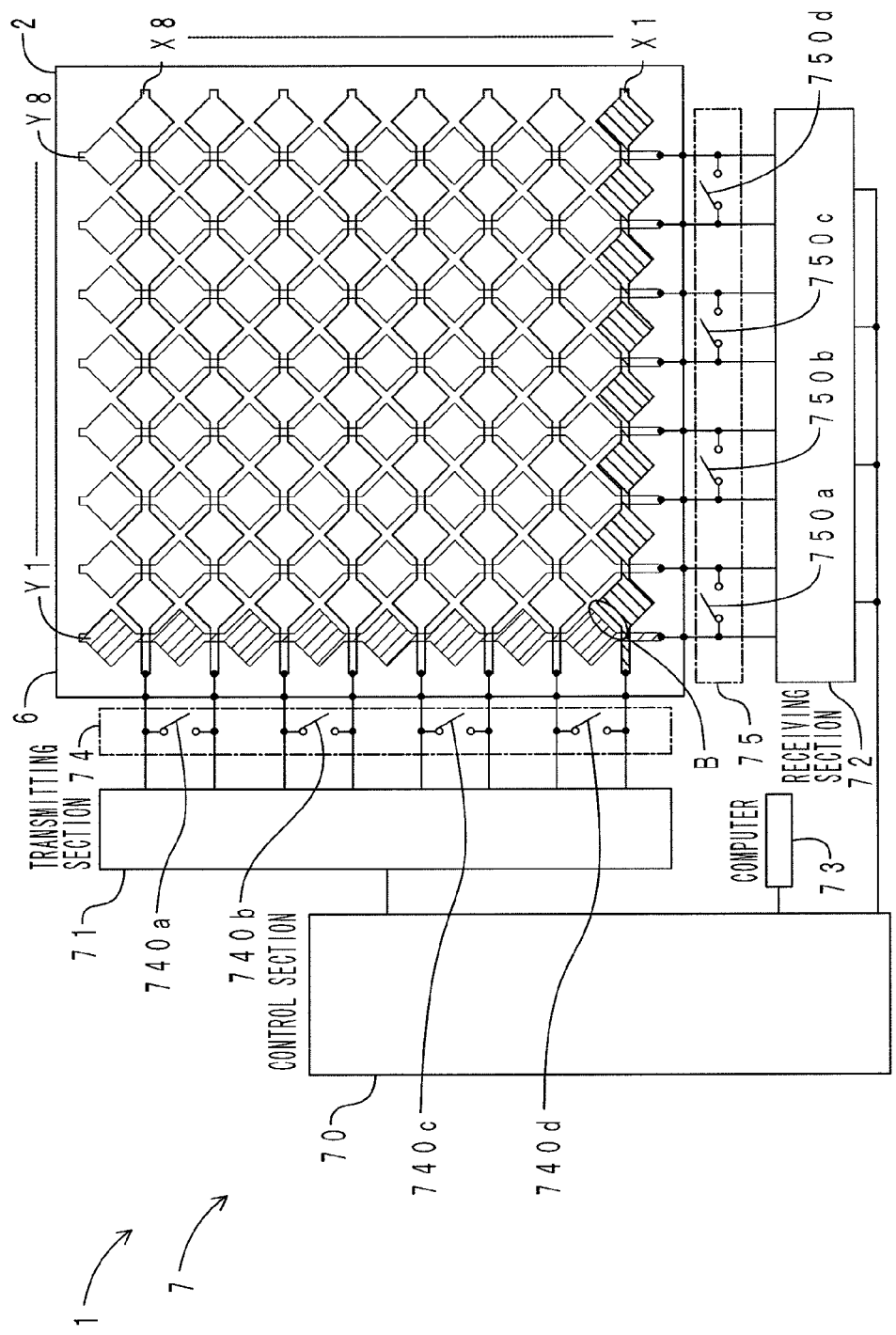
FIG. 9 is a block diagram of a hybrid sensor of a second embodiment in a decoupled state.
Figure 10:
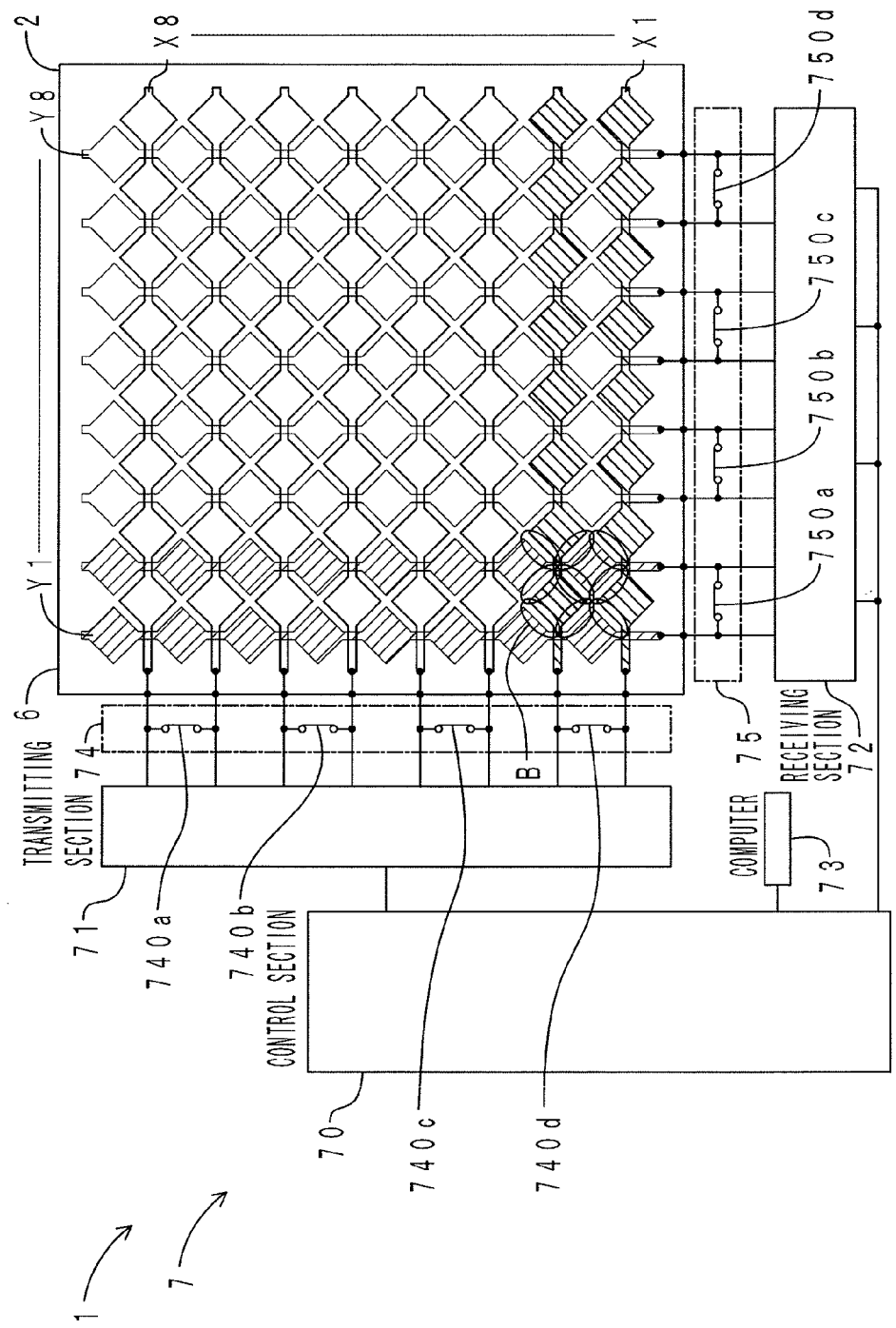
FIG. 10 is a block diagram of the hybrid sensor in a coupled state.

FIG. 9 is a block diagram showing the hybrid sensor of the present embodiment in a decoupled state. FIG. 10 is a block diagram showing this hybrid sensor in a coupled state. In these figures, the portions corresponding to those of FIG. 5 are denoted by the same reference characters.

As shown in FIGS. 9 and 10, a transmitting-side coupling section 74 is interposed between the transmitting section 71 and the first front-side electrodes X1 to X8. The transmitting-side coupling section 74 includes four switches 740a to 740d. The switch 740a is capable of coupling and decoupling the first front-side electrode X7 and the first front-side electrode X8 to and from each other. The switch 740b is capable of coupling and decoupling the first front-side electrode X5 and the first front-side electrode X6 to and from each other. The switch 740c is capable of coupling and decoupling the first front-side electrode X3 and the first front-side electrode X4 to and from each other. The switch 740d is capable of coupling and decoupling the first front-side electrode X1 and the first front-side electrode X2 to and from each other.

A receiving-side coupling section 75 is interposed between the receiving section 72 and the first back-side electrodes Y1 to Y8. The receiving-side coupling section 75 includes four switches 750a to 750d. The switch 750a is capable of coupling and decoupling the first back-side electrode Y1 and the first back-side electrode Y2 to and from each other. The switch 750b is capable of coupling and decoupling the first back-side electrode Y3 and the first back-side electrode Y4 to and from each other. The switch 750c is capable of coupling and decoupling the first back-side electrode Y5 and the first back-side electrode Y6 to and from each other. The switch 750d is capable of coupling and decoupling the first back-side electrode Y7 and the first back-side electrode Y8 to and from each other.

The hybrid sensor 1 of the present embodiment and the hybrid sensor of the first embodiment have similar functions and effects regarding the portions having common configurations. As shown in FIG. 9, all the switches 740a to 740d and 750a to 750d are opened in the decoupled state. A voltage is therefore sequentially supplied to the first front-side electrodes X1 to X8 in a scanning manner. This improves detection accuracy of the coordinates of the finger.

On the other hand, as shown in FIG. 10, all the switches 740a to 740d and 750a to 750d are closed in the coupled state. Each pair of adjoining ones of the first front-side electrodes X1 to X8 are therefore coupled by the switches 740a to 740d. Similarly, each pair of adjoining ones of the first back-side electrodes Y1 to Y8 are coupled by the switches 750a to 750d. A voltage is thus sequentially supplied to the first front-side electrodes X1 to X8 two by two in a scanning manner. This can increase initial (the state where an object to be detected is not approaching) capacitance.

That is, as shown in FIG. 9, in the decoupled state, a voltage is individually supplied to the first front-side electrodes X1 to X8, and a current is individually output from the first back-side electrodes Y1 to Y8. For example, in the case where a voltage is applied between the first front-side electrode X1 and the first back-side electrode Y1 as shown by hatched regions, an electric field B is generated at only one location.

On the other hand, as shown in FIG. 10, in the coupled state, a voltage is supplied to the first front-side electrodes X1 to X8 two by two, and a current is output from the first back-side electrodes Y1 to Y8 two by two. For example, in the case where a voltage is applied between the first front-side electrodes X1, X2 and the first back-side electrodes Y1, Y2 as shown by hatched regions, an electric field B is generated at a total of nine locations. This can increase initial capacitance in the coupled state, and thus can improve detection accuracy of the approach of the finger.

Third Embodiment

A hybrid sensor of the present embodiment is different from that of the first embodiment in that insulating spacers having load spread suppressing grooves are disposed on the upper and lower sides of the intermediate layer. Only the difference between the first and third embodiments will be described below.

Figure 11:
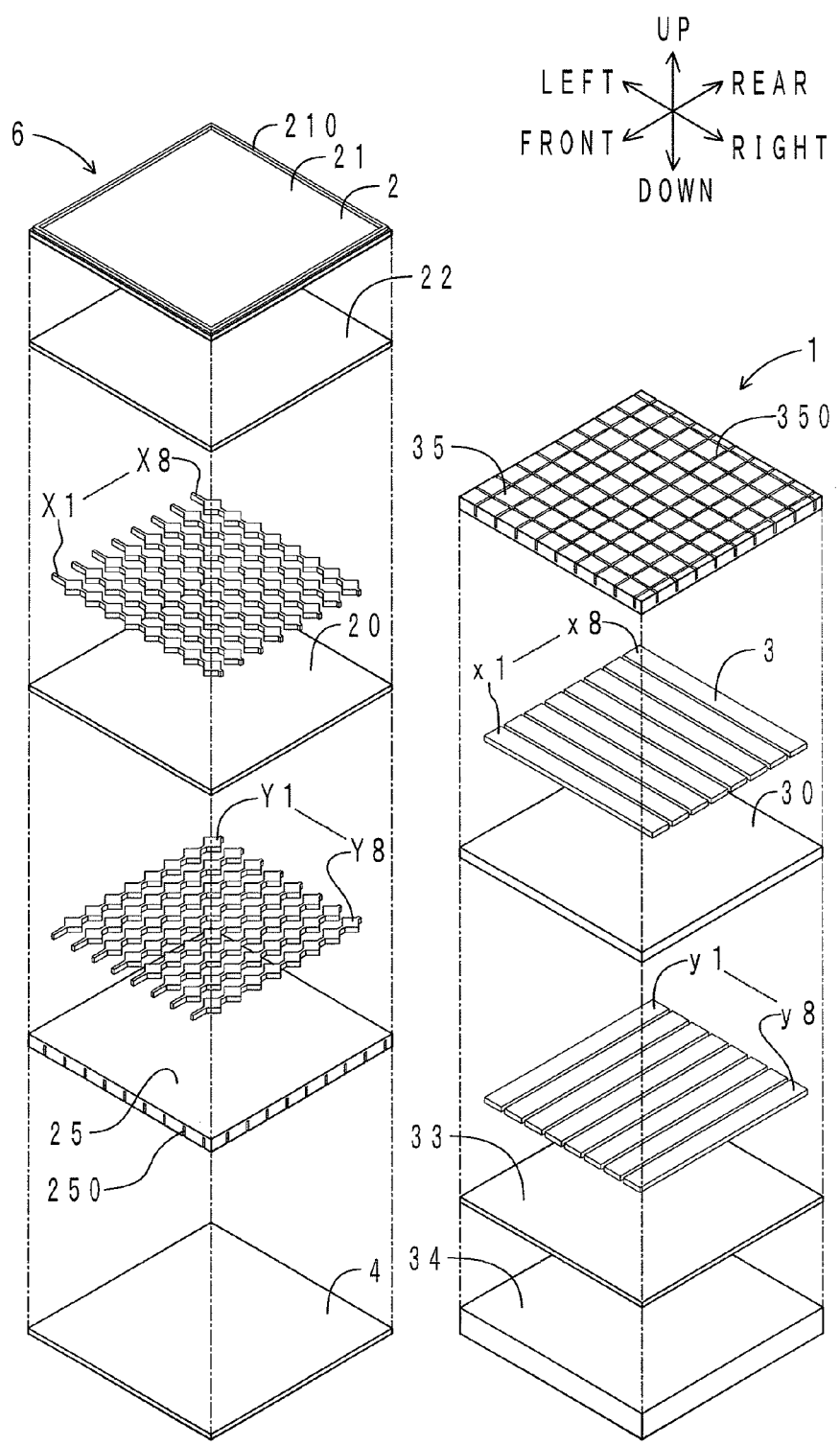
FIG. 11 is an exploded perspective view of a hybrid sensor of a third embodiment.
Figure 12:
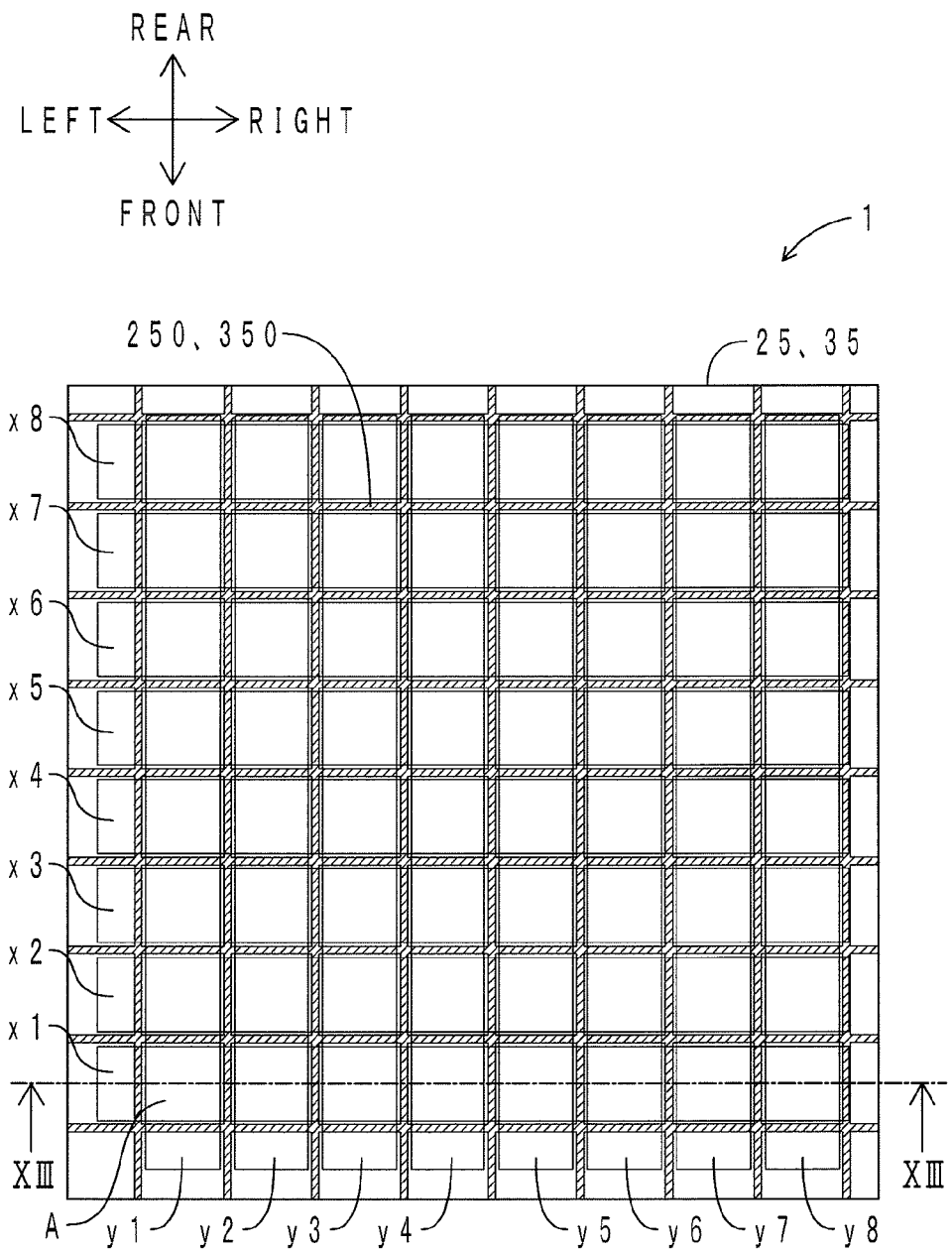
FIG. 12 is a transparent top view of a pair of insulating spacers and the components located below the insulating spacers in the hybrid sensor.
Figure 13:
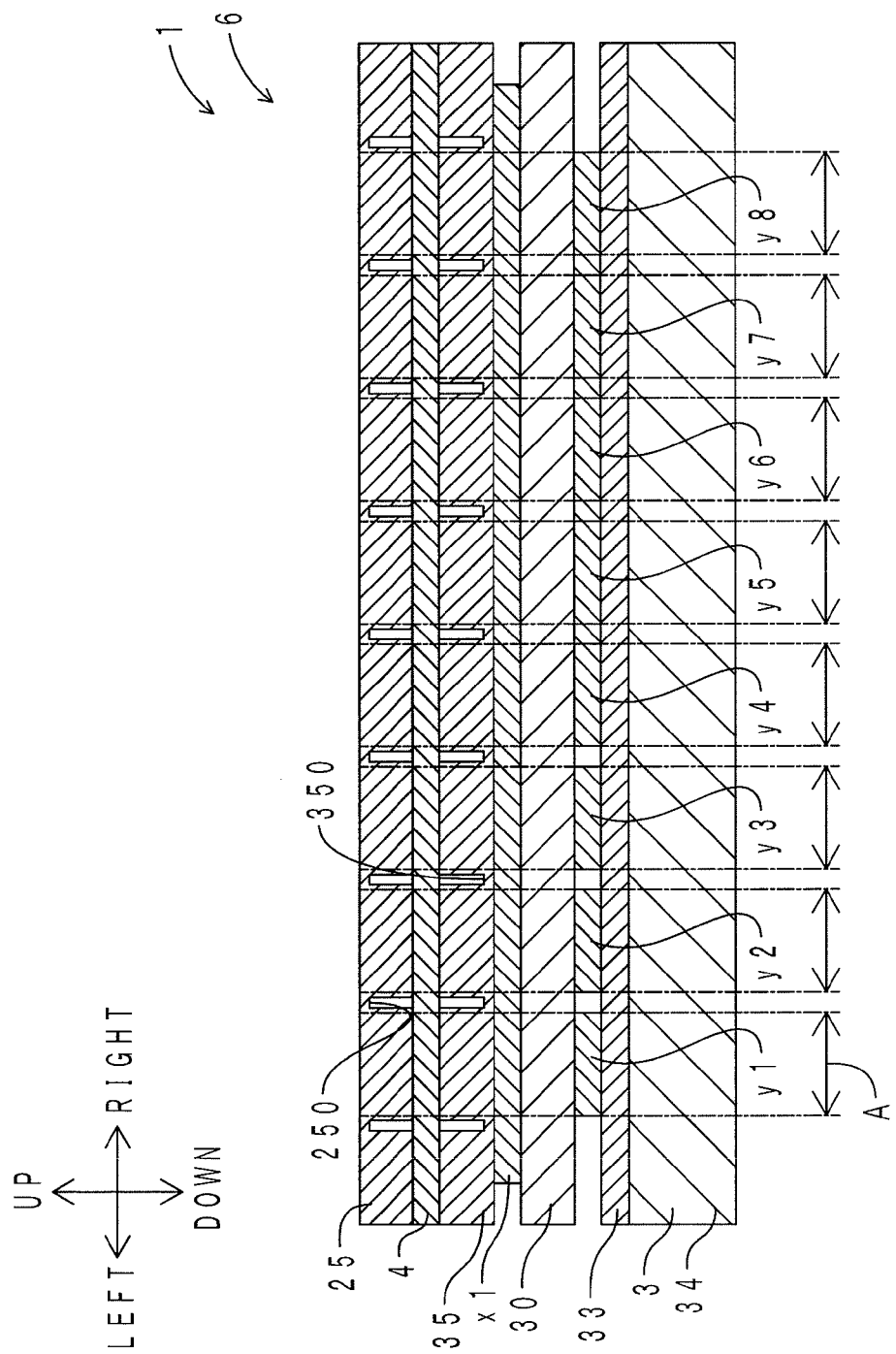
FIG. 13 is a sectional view taken along a direction XIII-XIII in FIG. 12.

FIG. 11 is an exploded perspective view of the hybrid sensor of the present embodiment. The portions corresponding to those of FIG. 1 are denoted by the same reference characters. FIG. 12 is a transparent top view of a pair of insulating spacers and the components located below the insulating spacers in the hybrid sensor. The portions corresponding to those of FIG. 3 are denoted by the same reference characters. Load spread suppressing grooves 250, 350 are hatched in the figure. FIG. 13 is a sectional view taken along a direction XIII-XIII in FIG. 12. The portions corresponding to those of FIG. 4 are denoted by the same reference characters.

As shown in FIGS. 11 to 13, insulating spacers 25, 35 are disposed on the upper and lower sides of the intermediate layer 4. Each of the insulating spacers 25, 35 is made of acrylic rubber, and is in the form of a square sheet. The insulating spacers 25, are elastic and have insulating properties.

The insulating spacer 25 is placed on the upper side of the intermediate layer 4. The insulating spacer 25 has a plurality of load spread suppressing grooves 250 in its lower surface. The plurality of load spread suppressing grooves 250 are formed in a grid pattern so as to surround each overlapping portion A. That is, each load spread suppressing groove 250 is interposed between horizontally adjoining ones of the overlapping portions A as viewed from above or below. The insulating spacer 25 has a planar upper surface. The insulating spacer 25 has the first back-side electrodes Y1 to Y8 printed (e.g., screen printed) on its upper surface.

The insulating spacer 35 is located on the lower side of the intermediate layer 4. The insulating spacer 35 has a plurality of load spread suppressing grooves 350 in its upper surface. The plurality of load spread suppressing grooves 350 are formed in a grid pattern so as to surround each overlapping portion A. That is, each load spread suppressing groove 350 is interposed between horizontally adjoining ones of the overlapping portions A as viewed from above or below. The insulating spacer 35 has a planar lower surface. The insulating spacer 35 has the second front-side electrodes x1 to x8 printed (e.g., screen printed) on its lower surface.

The hybrid sensor 1 of the present embodiment and the hybrid sensor of the first embodiment have similar functions and effects regarding the portions having common configurations. The insulating spacers 25, 35 are disposed on the upper and lower sides of the intermediate layer 4. This can increase the distance (interelectrode distance) in the top-bottom direction between the first back-side electrodes Y1 to Y8 of the proximity sensor section 2 and the second front-side electrodes x1 to x8 of the load sensor section 3. This can suppress generation of stray capacitance between the first back-side electrodes Y1 to Y8 and the second front-side electrodes x1 to x8, thereby increasing detection accuracy of the proximity sensor section 2 and the load sensor section 3.

The insulating spacers 25, 35 include the load spread suppressing grooves 250, 350. Each load spread suppressing groove 250, 350 is interposed between horizontally adjoining ones of the overlapping portions A as viewed from above or below. The insulating spacers 25, 35 are thinner in the top-bottom direction in the regions where the load spread suppressing grooves 250, 350 are formed than in the regions where the load spread suppressing grooves 250, 350 are not formed. This reduces the spring constant in the horizontal direction, and can therefore suppress spreading of the load in the horizontal direction. This increases detection accuracy of the coordinates in the horizontal direction, and also increases detection accuracy of the load.

The insulating spacer 25 has the first back-side electrodes Y1 to Y8 printed on its upper surface, and the insulating spacer 35 has the second front-side electrodes x1 to x8 printed on its lower surface. This facilitates assembly of the hybrid sensor 1 of the present embodiment.

Others

The embodiments of the hybrid sensor of the present invention are described above. However, embodiments are not limited to those described above, and various modifications and improvements can be made by those skilled in the art without departing from the spirit and scope of the invention.

For example, the type of the load sensor section 3 is not particularly limited. The load sensor section 3 may be a resistance change sensor that detects pressing based on a change (increase, decrease) in electric resistance, a load cell (strain gauge), a membrane switch that detects pressing based on whether electrical connection has been made or not, etc.

The mutual-capacitance sensor described above (the type in which capacitance between the first front-side electrodes X1 to X8 and the first back-side electrodes Y1 to Y8 decreases as an object to be detected approaches) can be used as the proximity sensor section 2. A self-capacitance sensor (the type in which the capacitance between the first front-side electrodes X1 to X8 and the first back-side electrodes Y1 to Y8 increases as the object to be detected approaches) may be used as the proximity sensor section 2.

The type of the object to be detected is not particularly limited. The object to be detected may be a palm, a toe, a chin, an elbow, a knee, a heel, an electrostatic pen, a glove, a sock, etc. The hybrid sensor of the present invention is elastic, and is therefore preferable in the case where a command is input by using a part of the body other than the finger 9.

In the above embodiments, as shown in FIG. 8, the DSP 700 determines "the fact that a small load is being applied from the finger 9 to the hybrid sensor 1, and the coordinates of the portion being subjected to the load," and "the fact that a large load is being applied from the finger 9 to the hybrid sensor 1, and the coordinates of the portion being subjected to the load," according to the state of the finger 9 with respect to the hybrid sensor 1. However, the DSP 700 may calculate the value of the load itself.

The pattern in which the first front-side electrodes X1 to X8 and the first back-side electrodes Y1 to Y8 are arranged is not particularly limited. The first front-side electrodes X1 to X8 and the first back-side electrodes Y1 to Y8 need only be arranged such that the wide portions X1a are arranged side by side in the planar direction as viewed from above or below, as shown in FIG. 2. The wide portions X1a may have a polygonal shape such as a hexagonal or octagonal shape, a circular shape, etc.

The pattern in which the second front-side electrodes x1 to x8 and the second back-side electrodes y1 to y8 are arranged is not particularly limited. The second front-side electrodes x1 to x8 and the second back-side electrodes y1 to y8 need only be arranged such that the overlapping portions A are formed between the second front-side electrodes x1 to x8 and the second back-side electrodes y1 to y8 as viewed from above or below, as shown in FIG. 3. For example, one of the second front-side electrodes x1 to x8 and the second back-side electrodes y1 to y8 may be arranged in a concentric circle pattern, and the other may be arranged in a radial pattern concentric with the pattern of the one of the second front-side electrodes x1 to x8 and the second back-side electrodes y1 to y8. In this case as well, the overlapping portions A can be formed between the second front-side electrodes x1 to x8 and the second back-side electrodes y1 to y8 as viewed from above or below.

The pattern of the protruding portion 210 of the protective layer 21 is not particularly limited. The protruding portion 210 may have a circular frame shape, a rectangular frame shape, a linear shape, a curved shape, a dot shape, etc. The present invention is not limited to the protruding portion 210, and a recessed portion may be formed in the protective layer 21.

In the above embodiment, the first front-side electrodes X1 to X8 and the first back-side electrodes Y1 to Y8 are screen printed on the first base material 20, and the second front-side electrodes x1 to x8 and the second back-side electrodes y1 to y8 are screen printed on the second base material 30. However, the first front-side electrodes X1 to X8 and the first back-side electrodes Y1 to Y8 may be arranged on the first base material 20 and the second front-side electrodes x1 to x8 and the second back-side electrodes y1 to y8 may be arranged on the second base material 30 by other printing methods such as an inkjet printing method, a flexo printing method, a gravure printing method, a pad printing method, lithography, and a dispenser printing method. The first front-side electrodes X1 to X8 and the first back-side electrodes Y1 to Y8 may be arranged on the first base material 20 and the second front-side electrodes x1 to x8 and the second back-side electrodes y1 to y8 may be arranged on the second base material 30 by other arrangement methods such as adhesion, bonding, molding, etc.

The first front-side electrodes X1 to X8 may be printed on the first front-side insulating layer 22, the first back-side electrodes Y1 to Y8 may be printed on the first back-side insulating layer 23, and then the first front-side insulating layer 22, the first base material 20, and the first back-side insulating layer 23 may be joined and bonded together. This method is effective in the case where the first front-side electrodes X1 to X8 and the first back-side electrodes Y1 to Y8 cannot be printed on the first base material 20 (e.g., in the case where the first base material 20 is made of a foam material). Similarly, the second front-side electrodes x1 to x8 may be printed on the second front-side insulating layer 32, the second back-side electrodes y1 to y8 may be printed on the second back-side insulating layer 33, and then the second front-side insulating layer 32, the second base material 30, and the second back-side insulating layer 33 may be joined and bonded together. This method is effective in the case where the second front-side electrodes x1 to x8 and the second back-side electrodes y1 to y8 cannot be printed on the second base material 30 (e.g., in the case where the second base material 30 is made of a foam material).

Figure 14:
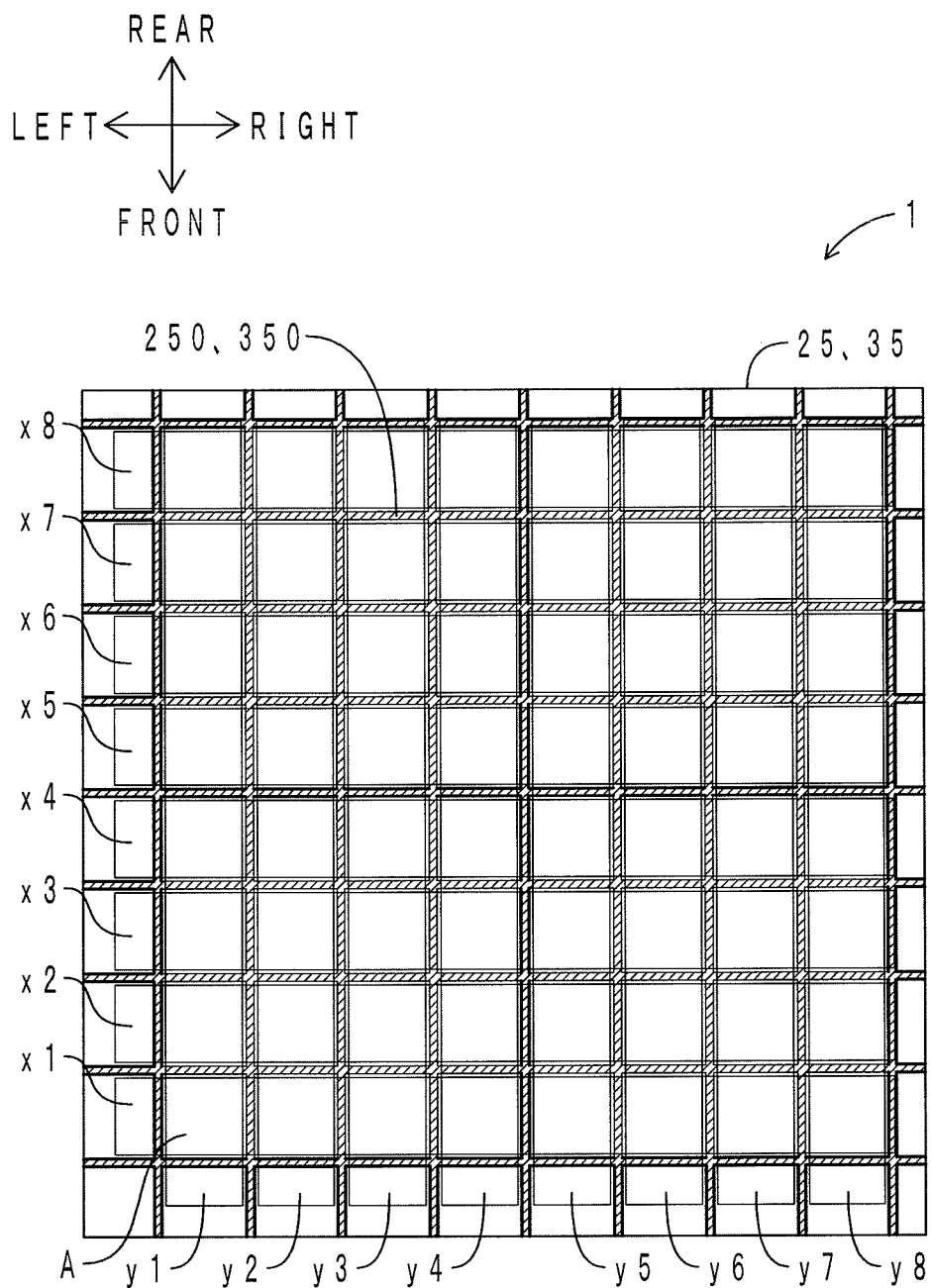
FIG. 14 is a top view of insulating spacers in a hybrid sensor of another embodiment (1).

The positions, number, and depth of the load spread suppressing grooves 250, 350 in the insulating spacers 25, 35 of the third embodiment are not particularly limited. FIG. 14 is a top view of insulating spacers in a hybrid sensor of another embodiment (1). The portions corresponding to those of FIG. 12 are denoted by the same reference characters. Thick lines show deep load spread suppressing grooves 250, 350, and thin lines show shallow load spread suppressing grooves 250, 350. As shown in FIG. 14, the deep load spread suppressing grooves 250, 350 may be arranged so as to divide a total of 64 overlapping portions A into four equal parts of 16 each. The deeper the load spread suppressing grooves 250, 350 are, the thinner the portions where the load spread suppressing grooves 250, 350 are formed are in the top-bottom direction. This reduces the spring constant in the horizontal direction, and can therefore suppress spreading of the load in the horizontal direction.

Figure 15:
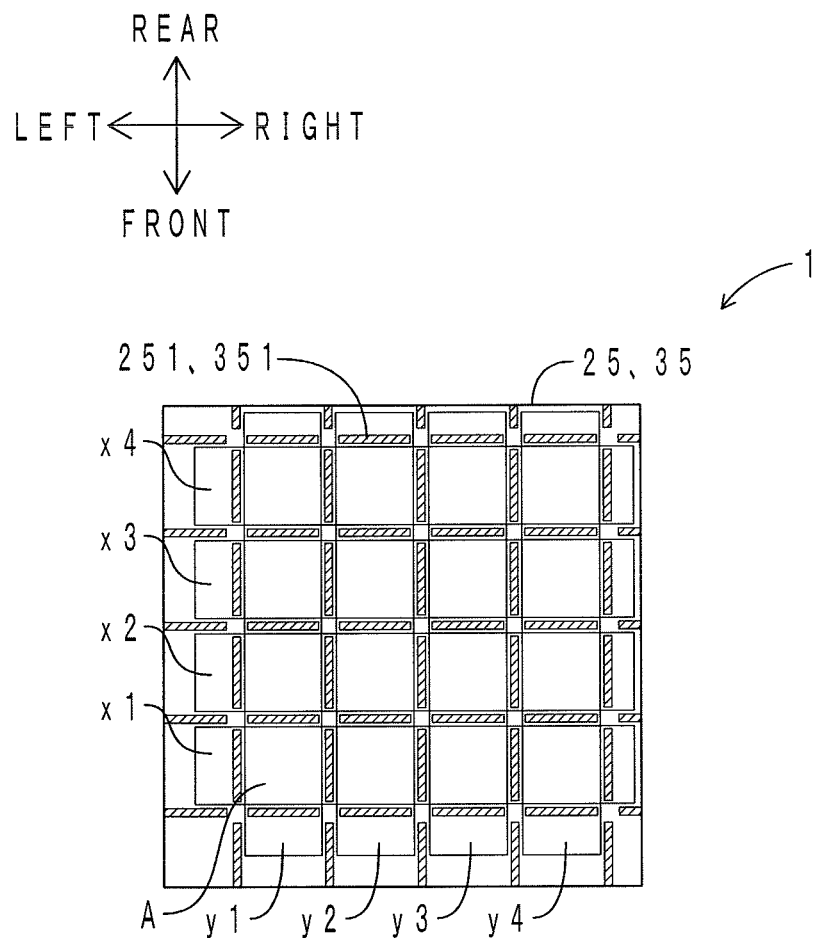
FIG. 15 is a top view of insulating spacers in a hybrid sensor of still another embodiment (2).
Figure 16:
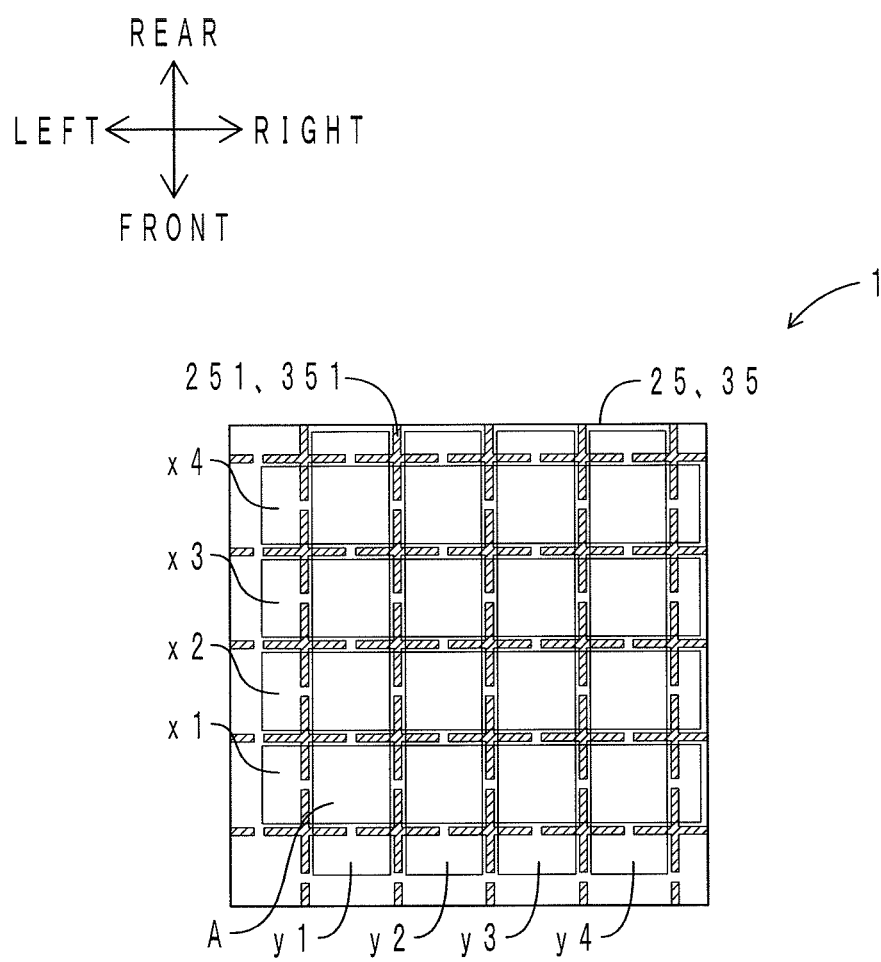
FIG. 16 is a top view of insulating spacers in a hybrid sensor of a further embodiment (3).

FIG. 15 is a top view of insulating spacers in a hybrid sensor of still another embodiment (2). FIG. 16 is a top view of insulating spacers in a hybrid sensor of a further embodiment (3). In these figures, the portions corresponding to those of FIG. 12 are denoted by the same reference characters. As shown by hatched regions in FIGS. 15 and 16, the load spread suppressing grooves may be replaced with load spread suppressing holes 251, 351. The load spread suppressing holes 251, 351 are in the shape of a long hole. The load spread suppressing holes 251, 351 extend through the insulating spacers 25, 35 in the top-bottom direction. The insulating spacers 25, 35 have a smaller spring constant in the horizontal direction in the regions where the load spread suppressing holes 251, 351 are formed than in the regions where the load spread suppressing holes 251, 351 are not formed. This can suppress spreading of the load in the horizontal direction.

The load spread suppressing grooves 250, 350 shown in FIGS. 12 and 14 may be combined with the load spread suppressing holes 251, 351 shown in FIGS. 15 and 16. For example, the load spread suppressing groove 250, 350 may be interposed between adjoining ones of the load spread suppressing holes 251, 351. The load spread suppressing grooves 250, 350 need only be disposed in at least one of the upper and lower surfaces of each insulating spacer 25, 35. The insulating spacers 25, 35 may be divided into individual pieces along the load spread suppressing grooves 250, 350 shown in FIG. 12.

The load spread suppressing grooves 250, 350 and the load spread suppressing holes 251, 351 may be arranged so as to surround groups of a plurality of overlapping portions A each. For example, only those load spread suppressing grooves 250, 350 which surround the groups of 16 overlapping portions A each as shown by solid lines in FIG. 14 may be provided.

The elastomer that is used for the first base material 20 and the second base material 30 is not particularly limited. The elastomer may contain at least one selected from silicone rubber, acrylonitrile-butadiene copolymer rubber, acrylic rubber, epichlorohydrin rubber, chlorosulfonated polyethylene, chlorinated polyethylene, and urethane rubber. This can increase the specific dielectric constant of the first base material 20 and the second base material 30, and therefore can increase capacitance.

The elastomer that is used for the first front-side electrodes X1 to X8, the first back-side electrodes Y1 to Y8, the second front-side electrodes x1 to x8, and the second back-side electrodes y1 to y8 is not particularly limited. The elastomer may contain silicone rubber, ethylene-propylene copolymer rubber, natural rubber, styrene-butadiene copolymer rubber, acrylonitrile-butadiene copolymer rubber, acrylic rubber, epichlorohydrin rubber, chlorosulfonated polyethylene, chlorinated polyethylene, urethane rubber, etc.

The conductive filler that is used for the first front-side electrodes X1 to X8, the first back-side electrodes Y1 to Y8, the second front-side electrodes x1 to x8, and the second back-side electrodes y1 to y8 is not particularly limited. The conductive filler may be made of at least one selected from a carbon material and a metal. Highly conductive silver, copper, etc. are preferable as the metal. Fine particles of silver, copper, etc. or fine particles having their surfaces plated with silver etc. can be used as the conductive filer. The carbon material has satisfactory conductive properties and is relatively inexpensive. The use of the conductive filler made of the carbon material can therefore reduce manufacturing cost of the hybrid sensor 1. Examples of the carbon material include conductive carbon black, carbon nanotube, a derivative of carbon nanotube, graphite, conductive carbon fiber, etc. In particular, conductive carbon black, graphite, and conductive carbon fiber have satisfactory conductive properties and relatively inexpensive. The use of these materials can therefore reduce the manufacturing cost of the hybrid sensor 1.

The elastomer that is used for the protective layer 21, the first front-side insulating layer 22, the first back-side insulating layer 23, the second front-side insulating layer 32, and the second back-side insulating layer 33 is not particularly limited. The elastomer may contain acrylic rubber, urethane rubber, silicone rubber, ethylene-propylene copolymer rubber, natural rubber, styrene-butadiene rubber, acrylonitrile-butadiene rubber, epichlorohydrin rubber, chlorosulfonated polyethylene, chlorinated polyethylene rubber, etc.

The material of the underlying layer 34 is not particularly limited. In the case of an elastomer, ethylene-propylene copolymer rubber etc. having a large amount of oil added thereto may be used. In the case of a foam material, polyethylene foam or polystyrene foam may be used. In the case of a three-dimensional knitted fiber fabric, a three-dimensional knitted fabric of fibers such as polyester fibers or polyamide fibers, or short fibers three-dimensionally thermally fusion-bonded to a fabric may be used.

A gel elastomer may be used as the material of the underlying layer 34. The gel elastomer is very elastic. Moreover, the gel elastomer has small hysteresis in a stress-strain curve. The gel elastomer therefore quickly returns to its original shape. This reduces the time required for a single input operation. The gel elastomer has a large tack force. Merely disposing the second back-side insulating layer 33 on the underlying layer 34 can therefore bond them together.

At least one selected from silicone gel, urethane gel, and a thermoplastic elastomer containing an oil component may be used as the gel elastomer for the underlying layer 34. This facilitates production of the underlying layer 34 having desired flexibility and restoration properties.

The thermoplastic elastomer containing an oil component desirably contains 70 mass % or more of the oil component with respect to the total mass (100 mass %). The thermoplastic elastomer desirably has a three-part structure of A-B-A, where A represents a rigid polymer (polystyrene, functional polymer, etc.), and B represents an elastomeric polymer (polybutylene, polyethylene, poly(ethylene/propylene), poly(ethylene-ethylene/propylene), hydrogenated poly (isoprene, butadiene, isoprene-butadiene), or poly(ethylene/butylene+ethylene/propylene)). A thermoplastic elastomer having an ultrahigh molecular polystyrene-poly(ethylene-ethylene/propylene)-polystyrene structure is particularly preferable. Examples of the oil component include paraffinic white mineral oil, paraffin, isoparaffin, naphthenic oil, polybutylene, polypropylene, polyterpene, poly-β-pinene, hydrogenated polybutane, and polybutane (having an epoxide group at one end of a polybutane polymer).

Fiber containing the conductive filler may be used as the conductive fiber for the intermediate layer 4. The intermediate layer 4 may be made of a woven fabric, a knitted fabric, a non-woven fabric, an elastomer, etc., or may be made of a woven fabric, a knitted fabric, a non-woven fabric, an elastomer, etc. having its outer surface coated with a conductive coating material.

The intermediate layer 4 itself may be made of, e.g., such a conductive coating material that is used for the first front-side electrodes X1 to X8, the first back-side electrodes Y1 to Y8, the second front-side electrodes x1 to x8, the second back-side electrodes y1 to y8. In this case, the intermediate layer 4 may be applied (e.g., screen printed) to the first back-side insulating layer 23, the second front-side insulating layer 32, the insulating spacer 25, and the insulating spacer 35.

The hybrid sensor of the present invention can be used as a touch panel, a touch screen, an input interface device, etc. of a smart phone, a personal computer, a mobile phone, a game machine, etc.

The invention claimed is:

1. A hybrid sensor, comprising:
a proximity sensor section that includes a first base material having insulating properties and made of an elastomer, a plurality of first front-side electrodes disposed on a front side of the first base material, having conductive properties, and made of an elastomer, a plurality of first back-side electrodes disposed on a back side of the first base material, having conductive properties, and made of an elastomer, and a protective layer disposed on a front side of the plurality of first front-side electrodes, having insulating properties, and made of an elastomer, and that detects approach and coordinates of an object to be detected, based on a change in capacitance between one of the plurality of first front-side electrodes and one of the plurality of first back-side electrodes which is caused by the approach of the object to be detected; and
a load sensor section that is disposed on a back side of the proximity sensor section, and that detects pressing and coordinates of the object to be detected, based on a load that is applied from the object to be detected via the proximity sensor section,
wherein
the load sensor section includes a second base material having insulating properties and made of an elastomer, a plurality of second front-side electrodes disposed on a front side of the second base material, having conductive properties, and made of an elastomer, and a plurality of second back-side electrodes disposed on a back side of the second base material, having conductive properties, and made of an elastomer, and detects the pressing and the coordinates of the object to be detected, based on an increase in capacitance between one of the plurality of second front-side electrodes and one of the plurality of second back-side electrodes which is caused as an interelectrode distance between the one of the plurality of second front-side electrodes and the one of the plurality of second back-side electrodes is decreased by the load.

2. The hybrid sensor according to claim 1, wherein
the proximity sensor section detects the approach and the coordinates of the object to be detected, based on a decrease in the capacitance between the one of the plurality of first front-side electrodes and the one of the plurality of first back-side electrodes which is caused as capacitance is generated between the one of the plurality of first front-side electrodes and the object to be detected by the approach of the object to be detected.

3. The hybrid sensor according to claim 1, further comprising:
an intermediate layer disposed between the proximity sensor section and the load sensor section, having conductive properties, and being elastic and grounded.

4. The hybrid sensor according to claim 3, wherein
an insulating spacer having insulating properties and made of an elastomer is disposed on at least one of front and back sides of the intermediate layer.

5. The hybrid sensor according to claim 4, wherein
the insulating spacer has a load spread suppressing mechanism that suppresses spreading of the load in a planar direction.

6. The hybrid sensor according to claim 5, wherein
the load sensor section has a plurality of overlapping portions where the plurality of second front-side electrodes overlap the plurality of second back-side electrodes as viewed from a front side or a back side, and
the load spread suppressing mechanism is interposed between the overlapping portions that adjoin each other in the planar direction, as viewed from the front side or the back side.

7. The hybrid sensor according to claim 5, wherein
the load spread suppressing mechanism is a load spread suppressing groove that is formed in a front or back surface of the insulating spacer.

8. The hybrid sensor according to claim 5, wherein
the load spread suppressing mechanism is a load spread suppressing hole that extends through the insulating spacer in a front-back direction.

9. The hybrid sensor according to claim 1, wherein
the proximity sensor section includes a first front-side insulating layer disposed on the front side of the plurality of first front-side electrodes and made of an elastomer, and a first back-side insulating layer disposed on a back side of the plurality of first back-side electrodes and made of an elastomer,
the load sensor section includes a second front-side insulating layer disposed on a front side of the plurality of second front-side electrodes and made of an elastomer, and a second back-side insulating layer disposed on a back side of the plurality of second back-side electrodes and made of an elastomer, and
the hybrid sensor satisfies at least one of the following (a) and (b):
(a) in the proximity sensor section, the first front-side electrodes are printed on at least one of the first base material and the first front-side insulating layer, and the first back-side electrodes are printed on at least one of the first base material and the first back-side insulating layer; and
(b) in the load sensor section, the second front-side electrodes are printed on at least one of the second base material and the second front-side insulating layer, and the second back-side electrodes are printed on at least one of the second base material and the second back-side insulating layer.

10. The hybrid sensor according to claim 1, wherein
at least one of a protruding portion and a recessed portion is disposed on a surface of the protective layer.

* * * * *